(12) United States Patent
Schweich, Jr. et al.

(10) Patent No.: US 8,267,852 B2
(45) Date of Patent: Sep. 18, 2012

(54) HEART WALL TENSION REDUCTION APPARATUS AND METHOD

(75) Inventors: Cyril J. Schweich, Jr., Maple Grove, MN (US); Robert M. Vidlund, Maplewood, MN (US); Todd J. Mortier, Minneapolis, MN (US)

(73) Assignee: Edwards Lifesciences, LLC, Irvine, CA (US)

( * ) Notice: Subject to any disclaimer, the term of this patent is extended or adjusted under 35 U.S.C. 154(b) by 0 days.

(21) Appl. No.: 12/832,507

(22) Filed: Jul. 8, 2010

(65) Prior Publication Data

US 2010/0274076 A1    Oct. 28, 2010

Related U.S. Application Data

(63) Continuation of application No. 10/127,731, filed on Apr. 23, 2002, now Pat. No. 7,883,539, which is a continuation-in-part of application No. 09/985,361, filed on Nov. 2, 2001, now Pat. No. 6,589,160, which is a continuation of application No. 09/697,597, filed on Oct. 27, 2000, now Pat. No. 6,332,864, which is a continuation of application No. 09/492,777, filed on Jan. 28, 2000, now Pat. No. 6,162,168, which is a continuation of application No. 08/778,277, filed on Jan. 2, 1997, now Pat. No. 6,050,936, said application No. 10/127,731 is a continuation-in-part of application No. 09/843,078, filed on Apr. 27, 2001, now Pat. No. 6,402,680, which is a continuation of application No. 09/522,068, filed on Mar. 9, 2000, now Pat. No. 6,264,602, which is a continuation of application No. 09/124,321, filed on Jul. 29, 1998, now Pat. No. 6,077,214.

(51) Int. Cl.
    *A61F 1/00* (2006.01)
(52) U.S. Cl. ......................................................... 600/37
(58) Field of Classification Search ..................... 600/37
    See application file for complete search history.

(56) References Cited

U.S. PATENT DOCUMENTS

| | | | |
|---|---|---|---|
| 963,899 | A | 7/1910 | Kistler |
| 3,019,790 | A | 2/1962 | Militana |
| 3,656,185 | A | 4/1972 | Carpentier |
| 3,980,068 | A | 9/1976 | Karsten et al. |
| 4,035,849 | A | 7/1977 | Angell et al. |
| 4,055,861 | A | 11/1977 | Carpentier et al. |
| 4,192,293 | A | 3/1980 | Asrican |
| 4,217,665 | A | 8/1980 | Bex et al. |

(Continued)

FOREIGN PATENT DOCUMENTS

DE    32 27 984 A1    2/1984

(Continued)

OTHER PUBLICATIONS

Alonso-Lej, *The Journal of Thoracic and Cardiovascular Surgery*, vol. 68, No. 3, Sep. 1974, p. 349.

(Continued)

*Primary Examiner* — Scott Getzow
(74) *Attorney, Agent, or Firm* — Melinda R. Michalerya

(57) ABSTRACT

Devices and methods for treatment of a failing heart by reducing the heart wall stress. The device can be one which reduces wall stress throughout the cardiac cycle or only a portion of the cardiac cycle.

6 Claims, 13 Drawing Sheets

U.S. PATENT DOCUMENTS

| | | |
|---|---|---|
| 4,261,342 A | 4/1981 | Aranguren Duo |
| 4,281,659 A | 8/1981 | Farrar et al. |
| 4,300,564 A | 11/1981 | Furihata |
| 4,306,319 A | 12/1981 | Kaster |
| 4,343,048 A | 8/1982 | Ross et al. |
| 4,372,293 A | 2/1983 | Vijil-Rosales |
| 4,409,974 A | 10/1983 | Freedland |
| 4,536,893 A | 8/1985 | Parravicini |
| 4,548,203 A | 10/1985 | Tacker, Jr. et al. |
| 4,554,929 A | 11/1985 | Samson et al. |
| 4,579,120 A | 4/1986 | MacGregor |
| 4,592,342 A | 6/1986 | Salmasian |
| 4,629,459 A | 12/1986 | Ionescu et al. |
| 4,632,101 A | 12/1986 | Freedland |
| 4,690,134 A | 9/1987 | Snyders |
| 4,705,040 A | 11/1987 | Mueller et al. |
| 4,936,857 A | 6/1990 | Kulik |
| 4,944,753 A | 7/1990 | Burgess et al. |
| 4,960,424 A | 10/1990 | Grooters |
| 4,991,578 A | 2/1991 | Cohen |
| 4,997,431 A | 3/1991 | Isner et al. |
| 5,061,277 A | 10/1991 | Carpentier et al. |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,152,765 A | 10/1992 | Ross et al. |
| 5,156,621 A | 10/1992 | Navia et al. |
| 5,169,381 A | 12/1992 | Snyders |
| 5,192,314 A | 3/1993 | Daskalakis |
| 5,250,049 A | 10/1993 | Michael |
| 5,256,132 A | 10/1993 | Snyders |
| 5,258,015 A | 11/1993 | Li et al. |
| 5,284,488 A | 2/1994 | Sideris |
| 5,300,087 A | 4/1994 | Knoepfler |
| 5,312,642 A | 5/1994 | Chesterfield et al. |
| 5,350,399 A | 9/1994 | Erlebacher et al. |
| 5,360,444 A | 11/1994 | Kusuhara |
| 5,376,112 A | 12/1994 | Duran |
| 5,383,840 A | 1/1995 | Heilman et al. |
| 5,385,528 A | 1/1995 | Wilk |
| 5,389,096 A | 2/1995 | Aita et al. |
| 5,397,331 A | 3/1995 | Himpens et al. |
| 5,417,709 A | 5/1995 | Slater |
| 5,433,727 A | 7/1995 | Sideris |
| 5,445,600 A | 8/1995 | Abdulla |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,522,884 A | 6/1996 | Wright |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup, III |
| 5,607,471 A | 3/1997 | Seguin et al. |
| 5,655,548 A | 8/1997 | Nelson et al. |
| 5,665,092 A | 9/1997 | Mangiardi et al. |
| 5,674,279 A | 10/1997 | Wright et al. |
| 5,682,906 A | 11/1997 | Sterman et al. |
| 5,683,364 A | 11/1997 | Zadini et al. |
| 5,702,343 A | 12/1997 | Alferness |
| 5,713,954 A | 2/1998 | Rosenberg et al. |
| 5,718,725 A | 2/1998 | Sterman et al. |
| 5,738,649 A | 4/1998 | Macoviak |
| 5,755,783 A | 5/1998 | Stobie et al. |
| 5,758,663 A | 6/1998 | Wilk et al. |
| 5,766,234 A | 6/1998 | Chen et al. |
| 5,776,189 A | 7/1998 | Khalid |
| 5,800,334 A | 9/1998 | Wilk |
| 5,800,528 A | 9/1998 | Lederman et al. |
| 5,800,531 A | 9/1998 | Cosgrove et al. |
| 5,807,384 A | 9/1998 | Mueller |
| 5,814,097 A | 9/1998 | Sterman et al. |
| 5,824,066 A | 10/1998 | Gross |
| 5,824,069 A | 10/1998 | Lemole |
| 5,840,059 A | 11/1998 | March et al. |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,876,436 A | 3/1999 | Vanney et al. |
| 5,888,240 A | 3/1999 | Carpentier et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A | 10/1999 | Schweich, Jr. et al. |
| 5,961,539 A | 10/1999 | Northrup, III et al. |
| 5,961,549 A | 10/1999 | Nguyen et al. |
| 5,967,990 A | 10/1999 | Thierman et al. |
| 5,971,910 A | 10/1999 | Tsitlik et al. |
| 5,971,911 A | 10/1999 | Wilk |
| 5,972,022 A | 10/1999 | Huxel |
| 5,984,857 A | 11/1999 | Buck et al. |
| 5,984,917 A | 11/1999 | Fleischman et al. |
| 5,999,678 A | 12/1999 | Murphy-Chutorian et al. |
| 6,001,126 A | 12/1999 | Nguyen-Thien-Nhon |
| 6,019,722 A | 2/2000 | Spence et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,086,532 A | 7/2000 | Panescu et al. |
| 6,095,968 A | 8/2000 | Snyders |
| 6,102,944 A | 8/2000 | Huynh et al. |
| 6,110,100 A | 8/2000 | Talpade |
| 6,113,536 A | 9/2000 | Aboul-Hosn et al. |
| 6,113,636 A | 9/2000 | Ogle |
| 6,117,159 A | 9/2000 | Huebsch et al. |
| 6,120,520 A | 9/2000 | Saadat et al. |
| 6,123,662 A | 9/2000 | Alferness et al. |
| 6,125,852 A | 10/2000 | Stevens et al. |
| 6,126,590 A | 10/2000 | Alferness |
| 6,129,758 A | 10/2000 | Love |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,165,183 A | 12/2000 | Kuehn et al. |
| 6,169,922 B1 | 1/2001 | Alferness et al. |
| 6,174,279 B1 | 1/2001 | Girard |
| 6,174,332 B1 | 1/2001 | Loch et al. |
| 6,179,791 B1 | 1/2001 | Krueger |
| 6,182,664 B1 | 2/2001 | Cosgrove |
| 6,183,411 B1 * | 2/2001 | Mortier et al. .................. 600/16 |
| 6,183,512 B1 | 2/2001 | Howanec, Jr. et al. |
| 6,190,408 B1 | 2/2001 | Melvin |
| 6,193,648 B1 | 2/2001 | Krueger |
| 6,197,053 B1 | 3/2001 | Cosgrove et al. |
| 6,206,004 B1 | 3/2001 | Schmidt et al. |
| 6,206,820 B1 | 3/2001 | Kazi et al. |
| 6,210,432 B1 | 4/2001 | Solem et al. |
| 6,217,610 B1 | 4/2001 | Carpentier et al. |
| 6,221,013 B1 | 4/2001 | Panescu et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,518 B1 | 5/2001 | Grabek et al. |
| 6,231,561 B1 | 5/2001 | Frazier et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,102 B1 | 6/2001 | Jayaraman |

| Patent | Date | Inventor |
|---|---|---|
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,258,023 B1 | 7/2001 | Rogers et al. |
| 6,260,552 B1 | 7/2001 | Mortier et al. |
| 6,260,820 B1 | 7/2001 | Chowdhury |
| 6,261,222 B1 | 7/2001 | Schweich, Jr. |
| 6,264,602 B1 | 7/2001 | Mortier et al. |
| 6,266,550 B1 | 7/2001 | Selmon et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hoek et al. |
| 6,309,370 B1 | 10/2001 | Haim et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B2 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,343,605 B1 | 2/2002 | Lafontaine |
| 6,360,749 B1 * | 3/2002 | Jayaraman .................... 128/898 |
| 6,361,545 B1 | 3/2002 | Macoviak et al. |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 * | 6/2002 | Melvin ......................... 623/3.1 |
| 6,416,459 B1 | 7/2002 | Haindl |
| 6,419,669 B1 | 7/2002 | Frazier et al. |
| 6,423,051 B1 | 7/2002 | Kaplan et al. |
| 6,425,856 B1 | 7/2002 | Shapland et al. |
| 6,432,039 B1 | 8/2002 | Wardle |
| 6,432,059 B2 | 8/2002 | Hickey |
| 6,436,088 B2 | 8/2002 | Frazier et al. |
| 6,439,237 B1 | 8/2002 | Buckberg et al. |
| 6,443,949 B2 | 9/2002 | Altman |
| 6,450,171 B1 | 9/2002 | Buckberg et al. |
| 6,458,100 B2 | 10/2002 | Roue et al. |
| 6,461,366 B1 | 10/2002 | Seguin |
| 6,478,729 B1 | 11/2002 | Rogers et al. |
| 6,482,146 B1 | 11/2002 | Alferness et al. |
| 6,488,706 B1 | 12/2002 | Solymar |
| 6,494,825 B1 | 12/2002 | Talpade |
| 6,508,756 B1 | 1/2003 | Kung et al. |
| 6,511,426 B1 | 1/2003 | Hossack et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,537,314 B2 | 3/2003 | Langberg et al. |
| 6,544,167 B2 | 4/2003 | Buckberg et al. |
| 6,544,180 B1 | 4/2003 | Doten et al. |
| 6,547,821 B1 | 4/2003 | Taylor et al. |
| 6,569,198 B1 | 5/2003 | Wilson et al. |
| 6,572,529 B2 | 6/2003 | Wilk |
| 6,582,355 B2 | 6/2003 | Alferness et al. |
| 6,587,734 B2 | 7/2003 | Okuzumi |
| 6,589,160 B2 | 7/2003 | Schweich, Jr. et al. |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,278 B2 | 9/2003 | Kampichlet |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,619,291 B2 | 9/2003 | Hlavka |
| 6,622,730 B2 | 9/2003 | Ekvall et al. |
| 6,626,821 B1 | 9/2003 | Kung et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,656,221 B2 | 12/2003 | Taylor et al. |
| 6,663,558 B2 | 12/2003 | Lau et al. |
| 6,669,708 B1 | 12/2003 | Nissenbaum et al. |
| 6,673,009 B1 | 1/2004 | Vanden Hoek et al. |
| 6,676,702 B2 | 1/2004 | Mathis |
| 6,681,773 B2 | 1/2004 | Murphy et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,692,458 B2 | 2/2004 | Forman et al. |
| 6,695,768 B1 | 2/2004 | Levine et al. |
| 6,695,866 B1 | 2/2004 | Kuehn et al. |
| 6,701,929 B2 | 3/2004 | Hussein |
| 6,702,732 B1 | 3/2004 | Lau et al. |
| 6,702,763 B2 | 3/2004 | Murphy et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,712,804 B2 | 3/2004 | Roue et al. |
| 6,716,158 B2 | 4/2004 | Raman et al. |
| 6,719,767 B1 | 4/2004 | Kimblad |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,016 B1 | 5/2004 | Cox et al. |
| 6,733,525 B2 | 5/2004 | Yang et al. |
| 6,740,107 B2 | 5/2004 | Loeb et al. |
| 6,752,813 B2 | 6/2004 | Goldfarb et al. |
| 6,755,777 B2 | 6/2004 | Schweich, Jr. et al. |
| 6,755,779 B2 | 6/2004 | Vanden Hoek et al. |
| 6,767,362 B2 | 7/2004 | Schreck |
| 6,769,434 B2 | 8/2004 | Liddicoat et al. |
| 6,776,754 B1 | 8/2004 | Wilk |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,814,700 B1 | 11/2004 | Mueller et al. |
| 6,824,562 B2 | 11/2004 | Mathis et al. |
| 6,837,247 B2 | 1/2005 | Buckberg et al. |
| 6,846,296 B1 | 1/2005 | Milbocker et al. |
| 6,875,224 B2 | 4/2005 | Grimes |
| 6,876,887 B2 | 4/2005 | Okuzumi |
| 6,881,185 B2 | 4/2005 | Vanden Hoek et al. |
| 6,887,192 B1 | 5/2005 | Whayne et al. |
| 6,890,353 B2 | 5/2005 | Cohn et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,908,426 B2 | 6/2005 | Shapland et al. |
| 6,908,478 B2 | 6/2005 | Alferness et al. |
| 6,913,608 B2 | 7/2005 | Liddicoat et al. |
| 6,918,917 B1 | 7/2005 | Nguyen et al. |
| 6,921,407 B2 | 7/2005 | Nguyen et al. |
| 6,949,122 B2 | 9/2005 | Adams et al. |
| 6,951,534 B2 | 10/2005 | Girard et al. |
| 6,955,689 B2 | 10/2005 | Ryan et al. |
| 6,959,711 B2 | 11/2005 | Murphy et al. |
| 6,960,229 B2 | 11/2005 | Mathis et al. |
| 6,962,605 B2 | 11/2005 | Cosgrove et al. |
| 6,966,926 B2 | 11/2005 | Mathis |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,994,093 B2 | 2/2006 | Murphy et al. |
| 6,997,865 B2 | 2/2006 | Alferness et al. |
| 6,997,951 B2 | 2/2006 | Solem et al. |
| 7,004,958 B2 | 2/2006 | Adams et al. |

| | | |
|---|---|---|
| 7,011,682 B2 | 3/2006 | Lashinski et al. |
| 7,022,064 B2 | 4/2006 | Alferness et al. |
| 7,025,719 B2 | 4/2006 | Alferness et al. |
| 7,037,334 B1 | 5/2006 | Hlavka et al. |
| 7,044,967 B1 | 5/2006 | Solem et al. |
| 7,052,487 B2 | 5/2006 | Cohn et al. |
| 7,056,280 B2 | 6/2006 | Buckberg et al. |
| 7,060,021 B1 | 6/2006 | Wilk |
| 7,063,722 B2 | 6/2006 | Marquez |
| 7,070,618 B2 | 7/2006 | Streeter |
| 7,090,695 B2 | 8/2006 | Solem et al. |
| 7,112,207 B2 | 9/2006 | Allen et al. |
| 7,115,110 B2 | 10/2006 | Frazier et al. |
| 7,125,420 B2 | 10/2006 | Rourke et al. |
| 7,153,258 B2 | 12/2006 | Alferness et al. |
| 7,163,507 B2 | 1/2007 | Alferness |
| 7,166,071 B2 | 1/2007 | Alferness |
| 7,166,126 B2 | 1/2007 | Spence et al. |
| 7,179,282 B2 | 2/2007 | Alferness et al. |
| 7,186,264 B2 | 3/2007 | Liddicoat et al. |
| 7,189,199 B2 | 3/2007 | McCarthy et al. |
| 7,192,442 B2 | 3/2007 | Solem et al. |
| 7,214,181 B2 | 5/2007 | Shapland et al. |
| 7,220,277 B2 | 5/2007 | Arru et al. |
| 7,226,467 B2 | 6/2007 | Lucatero et al. |
| 7,229,469 B1 | 6/2007 | Witzel et al. |
| 7,241,310 B2 | 7/2007 | Taylor et al. |
| 7,252,632 B2 | 8/2007 | Shapland et al. |
| 7,255,674 B2 | 8/2007 | Alferness |
| 7,261,684 B2 | 8/2007 | Alferness |
| 7,264,587 B2 | 9/2007 | Chin |
| 7,270,676 B2 | 9/2007 | Alferness et al. |
| 7,275,546 B2 | 10/2007 | Buckberg et al. |
| 7,278,964 B2 | 10/2007 | Alferness |
| 7,291,168 B2 | 11/2007 | Macoviak et al. |
| 7,296,577 B2 | 11/2007 | Lashinski et al. |
| 7,309,354 B2 | 12/2007 | Mathis et al. |
| 7,311,728 B2 | 12/2007 | Solem et al. |
| 7,311,729 B2 | 12/2007 | Mathis et al. |
| 7,311,731 B2 | 12/2007 | Lesniak et al. |
| 7,326,174 B2 | 2/2008 | Cox et al. |
| 7,329,280 B2 | 2/2008 | Bolling et al. |
| 7,351,200 B2 | 4/2008 | Alferness |
| 7,361,137 B2 | 4/2008 | Taylor et al. |
| 7,364,588 B2 | 4/2008 | Mathis et al. |
| 7,373,207 B2 | 5/2008 | Lattouf |
| 7,377,940 B2 | 5/2008 | Ryan et al. |
| 7,381,182 B2 | 6/2008 | Raman et al. |
| 7,381,220 B2 | 6/2008 | Macoviak et al. |
| 7,390,293 B2 | 6/2008 | Jayaraman |
| 7,410,461 B2 | 8/2008 | Lau et al. |
| 7,419,466 B2 | 9/2008 | Vanden Hoek et al. |
| 2001/0003986 A1 | 6/2001 | Cosgrove |
| 2001/0005787 A1 | 6/2001 | Oz et al. |
| 2001/0009976 A1 | 7/2001 | Panescu et al. |
| 2001/0014800 A1 | 8/2001 | Frazier et al. |
| 2001/0014811 A1 | 8/2001 | Hussein |
| 2001/0018611 A1 | 8/2001 | Solem et al. |
| 2001/0021874 A1 | 9/2001 | Carpentier et al. |
| 2001/0029314 A1 | 10/2001 | Alferness et al. |
| 2001/0034551 A1 | 10/2001 | Cox |
| 2001/0037123 A1 | 11/2001 | Hancock |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0041821 A1 | 11/2001 | Wilk |
| 2001/0041914 A1 | 11/2001 | Frazier et al. |
| 2001/0041915 A1 | 11/2001 | Roue et al. |
| 2001/0044568 A1 | 11/2001 | Langberg et al. |
| 2001/0047122 A1 | 11/2001 | Vanden Hoek et al. |
| 2001/0049492 A1 | 12/2001 | Frazier et al. |
| 2002/0007216 A1 | 1/2002 | Melvin |
| 2002/0013571 A1 | 1/2002 | Goldfarb et al. |
| 2002/0016628 A1 | 2/2002 | Langberg et al. |
| 2002/0019580 A1 | 2/2002 | Lau et al. |
| 2002/0022880 A1 | 2/2002 | Melvin |
| 2002/0026092 A1 | 2/2002 | Buckberg et al. |
| 2002/0026094 A1 | 2/2002 | Roth |
| 2002/0028981 A1 | 3/2002 | Lau et al. |
| 2002/0029783 A1 | 3/2002 | Stevens et al. |
| 2002/0032364 A1 | 3/2002 | Lau et al. |
| 2002/0042554 A1 | 4/2002 | Alferness et al. |
| 2002/0045798 A1 | 4/2002 | Lau et al. |
| 2002/0045799 A1 | 4/2002 | Lau et al. |
| 2002/0045800 A1 | 4/2002 | Lau et al. |
| 2002/0052538 A1 | 5/2002 | Lau et al. |
| 2002/0056461 A1 | 5/2002 | Jayaraman |
| 2002/0058855 A1 | 5/2002 | Schweich, Jr. et al. |
| 2002/0065449 A1 | 5/2002 | Wardle |
| 2002/0065465 A1 | 5/2002 | Panescu et al. |
| 2002/0065554 A1 | 5/2002 | Streeter |
| 2002/0068850 A1 | 6/2002 | Vanden Hoek et al. |
| 2002/0077532 A1 | 6/2002 | Gannoe et al. |
| 2002/0082647 A1 | 6/2002 | Alferness et al. |
| 2002/0087173 A1 | 7/2002 | Alferness et al. |
| 2002/0091296 A1 | 7/2002 | Alferness |
| 2002/0103511 A1 | 8/2002 | Alferness et al. |
| 2002/0103532 A1 | 8/2002 | Langberg et al. |
| 2002/0103533 A1 | 8/2002 | Langberg et al. |
| 2002/0111533 A1 | 8/2002 | Melvin |
| 2002/0111567 A1 | 8/2002 | Vanden Hoek et al. |
| 2002/0111636 A1 | 8/2002 | Fleischman et al. |
| 2002/0133055 A1 | 9/2002 | Haindl |
| 2002/0143250 A1 | 10/2002 | Panescu et al. |
| 2002/0151766 A1 | 10/2002 | Shapland et al. |
| 2002/0151961 A1 | 10/2002 | Lashinski et al. |
| 2002/0161275 A1 | 10/2002 | Schweich, Jr. et al. |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0169502 A1 | 11/2002 | Mathis |
| 2002/0169504 A1 | 11/2002 | Alferness et al. |
| 2002/0173694 A1 | 11/2002 | Mortier et al. |
| 2002/0183835 A1 | 12/2002 | Taylor et al. |
| 2002/0183836 A1 | 12/2002 | Liddicoat et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2002/0188350 A1 | 12/2002 | Arru et al. |
| 2003/0004396 A1 | 1/2003 | Vanden Hock et al. |
| 2003/0009081 A1 | 1/2003 | Rogers et al. |
| 2003/0023132 A1 | 1/2003 | Melvin et al. |
| 2003/0028077 A1 | 2/2003 | Alferness et al. |
| 2003/0032979 A1 | 2/2003 | Mortier et al. |
| 2003/0045771 A1 | 3/2003 | Schweich, Jr. et al. |
| 2003/0045776 A1 | 3/2003 | Alferness et al. |
| 2003/0045896 A1 | 3/2003 | Murphy et al. |
| 2003/0050529 A1 | 3/2003 | Vidlund et al. |
| 2003/0050659 A1 | 3/2003 | Murphy et al. |
| 2003/0060674 A1 | 3/2003 | Gifford, III et al. |
| 2003/0065248 A1 | 4/2003 | Lau et al. |
| 2003/0069467 A1 | 4/2003 | Lau et al. |
| 2003/0078465 A1 | 4/2003 | Pai et al. |
| 2003/0078653 A1 | 4/2003 | Vesely et al. |
| 2003/0078671 A1 | 4/2003 | Lesniak et al. |
| 2003/0093104 A1 | 5/2003 | Bonner et al. |
| 2003/0105519 A1 | 6/2003 | Fasol et al. |
| 2003/0120340 A1 | 6/2003 | Liska et al. |
| 2003/0130730 A1 | 7/2003 | Cohn et al. |
| 2003/0130731 A1 | 7/2003 | Vidlund et al. |
| 2003/0135267 A1 | 7/2003 | Solem et al. |
| 2003/0144697 A1 | 7/2003 | Mathis et al. |
| 2003/0149333 A1 | 8/2003 | Alferness |
| 2003/0153946 A1 | 8/2003 | Kimblad |
| 2003/0158570 A1 | 8/2003 | Ferrazzi |
| 2003/0166992 A1 | 9/2003 | Schweich, Jr. et al. |
| 2003/0171641 A1 | 9/2003 | Schweich, Jr. et al. |
| 2003/0171776 A1 | 9/2003 | Adams et al. |
| 2003/0171806 A1 | 9/2003 | Mathis et al. |
| 2003/0181928 A1 | 9/2003 | Vidlund et al. |
| 2003/0191538 A1 | 10/2003 | Buckberg et al. |
| 2003/0199733 A1 | 10/2003 | Shapland et al. |
| 2003/0212453 A1 | 11/2003 | Mathis et al. |
| 2003/0225454 A1 | 12/2003 | Mathis et al. |
| 2003/0233022 A1 | 12/2003 | Vidlund et al. |
| 2003/0236569 A1 | 12/2003 | Mathis et al. |
| 2004/0002719 A1 | 1/2004 | Oz et al. |

| | | | | | |
|---|---|---|---|---|---|
| 2004/0003819 A1 | 1/2004 | St. Goar et al. | 2005/0113811 A1 | 5/2005 | Houser et al. |
| 2004/0010305 A1 | 1/2004 | Alferness et al. | 2005/0119519 A9 | 6/2005 | Girard et al. |
| 2004/0019377 A1 | 1/2004 | Taylor et al. | 2005/0131533 A1 | 6/2005 | Alfieri et al. |
| 2004/0019378 A1 | 1/2004 | Hlavka et al. | 2005/0149179 A1 | 7/2005 | Mathis et al. |
| 2004/0024286 A1 | 2/2004 | Melvin | 2005/0149180 A1 | 7/2005 | Mathis et al. |
| 2004/0030382 A1 | 2/2004 | St. Goar et al. | 2005/0149182 A1 | 7/2005 | Alferness et al. |
| 2004/0039442 A1 | 2/2004 | St. Goar et al. | 2005/0187619 A1 | 8/2005 | Mathis et al. |
| 2004/0039443 A1 | 2/2004 | Solem et al. | 2005/0197528 A1 | 9/2005 | Vanden Hoek et al. |
| 2004/0049115 A1 | 3/2004 | Murphy et al. | 2005/0197692 A1 | 9/2005 | Pai et al. |
| 2004/0049116 A1 | 3/2004 | Murphy et al. | 2005/0197693 A1 | 9/2005 | Pai et al. |
| 2004/0059181 A1 | 3/2004 | Alferness | 2005/0209690 A1 | 9/2005 | Mathis et al. |
| 2004/0059182 A1 | 3/2004 | Alferness | 2005/0216077 A1 | 9/2005 | Mathis et al. |
| 2004/0059187 A1 | 3/2004 | Alferness | 2005/0228217 A1 | 10/2005 | Alferness et al. |
| 2004/0059188 A1 | 3/2004 | Alferness | 2005/0261704 A1 | 11/2005 | Mathis |
| 2004/0059189 A1 | 3/2004 | Alferness | 2005/0267574 A1 | 12/2005 | Cohn et al. |
| 2004/0064014 A1 | 4/2004 | Melvin et al. | 2005/0272969 A1 | 12/2005 | Alferness et al. |
| 2004/0073302 A1 | 4/2004 | Rourke et al. | 2006/0004443 A1 | 1/2006 | Liddicoat et al. |
| 2004/0092962 A1 | 5/2004 | Thornton et al. | 2006/0009842 A1 | 1/2006 | Huynh et al. |
| 2004/0093023 A1 | 5/2004 | Allen et al. | 2006/0020336 A1 | 1/2006 | Liddicoat et al. |
| 2004/0102678 A1 | 5/2004 | Haindl | 2006/0025856 A1 | 2/2006 | Ryan et al. |
| 2004/0102679 A1 | 5/2004 | Alferness et al. | 2006/0030866 A1 | 2/2006 | Schreck |
| 2004/0102839 A1 | 5/2004 | Cohn et al. | 2006/0030882 A1 | 2/2006 | Adams et al. |
| 2004/0102840 A1 | 5/2004 | Solem et al. | 2006/0041306 A1 | 2/2006 | Vidlund et al. |
| 2004/0111101 A1 | 6/2004 | Chin | 2006/0052868 A1 | 3/2006 | Mortier et al. |
| 2004/0127983 A1 | 7/2004 | Mortier et al. | 2006/0064115 A1 | 3/2006 | Allen et al. |
| 2004/0133063 A1 | 7/2004 | McCarthy et al. | 2006/0064116 A1 | 3/2006 | Allen et al. |
| 2004/0133069 A1 | 7/2004 | Shapland et al. | 2006/0064118 A1 | 3/2006 | Kimblad |
| 2004/0152947 A1 | 8/2004 | Schroeder et al. | 2006/0069430 A9 | 3/2006 | Rahdert et al. |
| 2004/0158123 A1 | 8/2004 | Jayaraman | 2006/0106456 A9 | 5/2006 | Machold et al. |
| 2004/0162610 A1 | 8/2004 | Liska et al. | 2006/0111607 A1 | 5/2006 | Alferness et al. |
| 2004/0167374 A1 | 8/2004 | Schweich et al. | 2006/0116756 A1 | 6/2006 | Solem et al. |
| 2004/0167539 A1 | 8/2004 | Kuehn et al. | 2006/0116757 A1 | 6/2006 | Lashinski et al. |
| 2004/0171907 A1 | 9/2004 | Alferness et al. | 2006/0137697 A1 | 6/2006 | Murphy et al. |
| 2004/0171908 A1 | 9/2004 | Alferness et al. | 2006/0142854 A1 | 6/2006 | Alferness et al. |
| 2004/0171909 A1 | 9/2004 | Alferness | 2006/0149122 A1 | 7/2006 | Shapland et al. |
| 2004/0176678 A1 | 9/2004 | Murphy et al. | 2006/0149123 A1 | 7/2006 | Vidlund et al. |
| 2004/0176679 A1 | 9/2004 | Murphy et al. | 2006/0149368 A1 | 7/2006 | Spence |
| 2004/0176840 A1 | 9/2004 | Langberg et al. | 2006/0155165 A1 | 7/2006 | Vanden Hoek et al. |
| 2004/0181121 A1 | 9/2004 | Alferness et al. | 2006/0161040 A1 | 7/2006 | McCarthy et al. |
| 2004/0181122 A1 | 9/2004 | Alferness et al. | 2006/0173536 A1 | 8/2006 | Mathis et al. |
| 2004/0181123 A1 | 9/2004 | Alferness et al. | 2006/0184203 A1 | 8/2006 | Martin et al. |
| 2004/0181124 A1 | 9/2004 | Alferness | 2006/0184241 A1 | 8/2006 | Marquez |
| 2004/0181125 A1 | 9/2004 | Alferness et al. | 2006/0195012 A1 | 8/2006 | Mortier et al. |
| 2004/0181126 A1 | 9/2004 | Buckberg et al. | 2006/0212114 A1 | 9/2006 | Menicanti et al. |
| 2004/0186342 A1 | 9/2004 | Vanden Hock et al. | 2006/0229717 A1 | 10/2006 | Cohn et al. |
| 2004/0193260 A1 | 9/2004 | Alferness et al. | 2006/0235265 A1 | 10/2006 | Alferness et al. |
| 2004/0199183 A1 | 10/2004 | Oz et al. | 2006/0241340 A1 | 10/2006 | Schroeder et al. |
| 2004/0210304 A1 | 10/2004 | Seguin et al. | 2006/0247492 A1 | 11/2006 | Streeter |
| 2004/0225300 A1 | 11/2004 | Goldfarb et al. | 2006/0252984 A1 | 11/2006 | Rahdert et al. |
| 2004/0243229 A1 | 12/2004 | Vidlund et al. | 2006/0258900 A1 | 11/2006 | Buckberg et al. |
| 2004/0249452 A1 | 12/2004 | Adams et al. | 2007/0004962 A1 | 1/2007 | Alferness et al. |
| 2004/0267083 A1 | 12/2004 | McCarthy et al. | 2007/0038293 A1 | 2/2007 | St.Goar et al. |
| 2005/0004428 A1 | 1/2005 | Cox et al. | 2007/0050020 A1 | 3/2007 | Spence |
| 2005/0004666 A1 | 1/2005 | Alfieri et al. | 2007/0055303 A1 | 3/2007 | Vidlund et al. |
| 2005/0021056 A1 | 1/2005 | St. Goar et al. | 2007/0066879 A1 | 3/2007 | Mathis et al. |
| 2005/0021057 A1 | 1/2005 | St. Goar et al. | 2007/0100442 A1 | 5/2007 | Solem et al. |
| 2005/0021135 A1 | 1/2005 | Ryan et al. | 2007/0112244 A1 | 5/2007 | McCarthy et al. |
| 2005/0027351 A1 | 2/2005 | Reuter et al. | 2007/0118155 A1 | 5/2007 | Goldfarb et al. |
| 2005/0027353 A1 | 2/2005 | Alferness et al. | 2007/0129598 A1 | 6/2007 | Raman et al. |
| 2005/0027369 A1 | 2/2005 | Eldridge et al. | 2007/0129737 A1 | 6/2007 | Goldfarb et al. |
| 2005/0033419 A1 | 2/2005 | Alferness et al. | 2007/0156235 A1 | 7/2007 | Rourke et al. |
| 2005/0033446 A1 | 2/2005 | Deem et al. | 2007/0161846 A1 | 7/2007 | Nikolic et al. |
| 2005/0038507 A1 | 2/2005 | Alferness et al. | 2007/0208211 A1 | 9/2007 | Shapland et al. |
| 2005/0043792 A1 | 2/2005 | Solem et al. | 2007/0213814 A1 | 9/2007 | Liddicoat et al. |
| 2005/0049679 A1 | 3/2005 | Taylor et al. | 2007/0225547 A1 | 9/2007 | Alferness |
| 2005/0049698 A1 | 3/2005 | Bolling et al. | 2007/0288090 A1 | 12/2007 | Solem et al. |
| 2005/0060030 A1 | 3/2005 | Lashinski et al. | 2008/0033235 A1 | 2/2008 | Shapland et al. |
| 2005/0065598 A1 | 3/2005 | Mathis et al. | 2008/0051807 A1 | 2/2008 | St. Goar et al. |
| 2005/0065601 A1 | 3/2005 | Lee et al. | 2008/0091191 A1 | 4/2008 | Witzel et al. |
| 2005/0071000 A1 | 3/2005 | Liddicoat et al. | 2008/0097489 A1 | 4/2008 | Goldfarb et al. |
| 2005/0075723 A1 | 4/2005 | Schroeder et al. | 2008/0097593 A1 | 4/2008 | Bolling et al. |
| 2005/0075727 A1 | 4/2005 | Wheatley | 2008/0097594 A1 | 4/2008 | Mathis et al. |
| 2005/0080402 A1 | 4/2005 | Santamore et al. | 2008/0125622 A1 | 5/2008 | Walsh et al. |
| 2005/0080483 A1 | 4/2005 | Solem et al. | 2008/0140191 A1 | 6/2008 | Mathis et al. |
| 2005/0085688 A1 | 4/2005 | Girard et al. | 2008/0147184 A1 | 6/2008 | Lattouf |
| 2005/0095268 A1 | 5/2005 | Walsh et al. | 2008/0154359 A1 | 6/2008 | Salgo et al. |
| 2005/0096740 A1 | 5/2005 | Langberg et al. | 2008/0161638 A1 | 7/2008 | Taylor et al. |
| 2005/0107810 A1 | 5/2005 | Morales et al. | 2008/0167714 A1 | 7/2008 | St. Goar et al. |
| 2005/0113635 A1 | 5/2005 | Whayne et al. | 2008/0183194 A1 | 7/2008 | Goldfarb et al. |

| | | | |
|---|---|---|---|
| 2008/0183284 A1 | 7/2008 | Ryan et al. | |
| 2008/0188861 A1 | 8/2008 | Ryan et al. | |
| 2008/0195200 A1 | 8/2008 | Vidlund et al. | |
| 2008/0208331 A1 | 8/2008 | McCarthy et al. | |
| 2008/0215008 A1 | 9/2008 | Nance et al. | |

FOREIGN PATENT DOCUMENTS

| | | |
|---|---|---|
| DE | 36 14 292 | 11/1987 |
| DE | 42 34 127 | 5/1994 |
| DE | 295 00 381 U1 | 7/1995 |
| DE | 296 19 294 | 8/1997 |
| DE | 298 24 017 U1 | 6/1998 |
| DE | 198 26 675 | 3/1999 |
| DE | 199 47 885 | 4/2000 |
| EP | 0 583 012 | 2/1994 |
| EP | 0 792 621 A1 | 9/1997 |
| EP | 0 820 729 A1 | 1/1998 |
| EP | 1 129 736 A1 | 9/2001 |
| FR | 2 768 324 | 3/1999 |
| GB | 2214428 | 9/1989 |
| NL | 9 200 878 | 12/1993 |
| WO | 91/19465 | 12/1991 |
| WO | 95/06447 | 3/1995 |
| WO | 95/16476 | 6/1995 |
| WO | WO 95/16407 | 6/1995 |
| WO | 96/04852 | 2/1996 |
| WO | WO 96/02197 A1 | 2/1996 |
| WO | 96/40356 | 12/1996 |
| WO | WO 97/14286 | 4/1997 |
| WO | 97/24082 | 7/1997 |
| WO | 97/24083 | 7/1997 |
| WO | 97/24101 | 7/1997 |
| WO | WO 97/41779 A1 | 11/1997 |
| WO | 98/03213 | 1/1998 |
| WO | 98/14136 | 4/1998 |
| WO | WO 98/17347 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | WO 98/58598 | 12/1998 |
| WO | 99/00059 | 1/1999 |
| WO | 99/11201 | 3/1999 |
| WO | 99/13777 | 3/1999 |
| WO | WO 99/13936 | 3/1999 |
| WO | WO 99/16350 | 4/1999 |
| WO | WO 99/22784 | 5/1999 |
| WO | 99/30647 | 6/1999 |
| WO | 99/44534 | 9/1999 |
| WO | 99/44680 | 9/1999 |
| WO | WO 99/44969 | 9/1999 |
| WO | 99/52470 | 10/1999 |
| WO | WO 99/53977 | 10/1999 |
| WO | 99/56655 | 11/1999 |
| WO | WO 99/66969 | 12/1999 |
| WO | 00/02500 | 1/2000 |
| WO | WO 00/03759 | 1/2000 |
| WO | WO 00/06026 | 2/2000 |
| WO | WO 00/06028 | 2/2000 |
| WO | 00/13722 | 3/2000 |
| WO | 00/18320 | 4/2000 |
| WO | 00/27304 | 5/2000 |
| WO | 00/28912 | 5/2000 |
| WO | 00/28918 | 5/2000 |
| WO | WO 00/25842 | 5/2000 |
| WO | WO 00/25853 | 5/2000 |
| WO | 00/36995 | 6/2000 |
| WO | 00/42919 | 7/2000 |
| WO | WO 00/42950 | 7/2000 |
| WO | WO 00/42951 | 7/2000 |
| WO | 00/45735 | 8/2000 |
| WO | 00/62727 | 10/2000 |
| WO | WO 00/60995 | 10/2000 |
| WO | WO 00/61033 | 10/2000 |
| WO | WO 00/62715 | 10/2000 |
| WO | 01/03608 | 1/2001 |
| WO | WO 01/00111 | 1/2001 |
| WO | 01/21070 | 3/2001 |
| WO | 01/21098 | 3/2001 |
| WO | 01/21099 | 3/2001 |
| WO | WO 01/19291 | 3/2001 |
| WO | WO 01/19292 | 3/2001 |
| WO | WO 01/21247 A1 | 3/2001 |
| WO | WO 01/26557 | 4/2001 |
| WO | WO 01/28432 | 4/2001 |
| WO | WO 01/49217 A2 | 7/2001 |
| WO | WO 01/50981 | 7/2001 |
| WO | WO 01/54562 A2 | 8/2001 |
| WO | WO 01/54618 | 8/2001 |
| WO | WO 01/54745 | 8/2001 |
| WO | WO 01/67985 | 9/2001 |
| WO | WO 01/70116 | 9/2001 |
| WO | WO 01/78625 A1 | 10/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/11625 A2 | 2/2002 |
| WO | WO 02/13726 | 2/2002 |
| WO | WO 02/19917 A1 | 3/2002 |
| WO | WO 02/28450 A2 | 4/2002 |
| WO | WO 02/30292 | 4/2002 |
| WO | WO 02/30335 | 4/2002 |
| WO | WO 02/34167 A2 | 5/2002 |
| WO | WO 02/38081 A2 | 5/2002 |
| WO | WO 02/43617 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/064035 A1 | 8/2002 |
| WO | WO 02/076284 A2 | 10/2002 |
| WO | WO 02/078576 A2 | 10/2002 |
| WO | WO 02/085251 A1 | 10/2002 |
| WO | WO 02/096275 A2 | 12/2002 |
| WO | WO 03/001893 A2 | 1/2003 |
| WO | WO 03/007778 A2 | 1/2003 |
| WO | WO 03/015611 A2 | 2/2003 |
| WO | WO 03/022131 A2 | 3/2003 |
| WO | WO 03/059209 A2 | 7/2003 |

OTHER PUBLICATIONS

Hayden et al., "Scintiphotographic Studies of Acquired Cardiovascular Disease," *Seminars in Nuclear Medicine*, vol. III, No. 2, Apr. 1973, pp. 177-190.

Timek, Tomasz A. et al., Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002.

Edie, M.D. et al., "Surgical repair of single ventricle,"*The Journal of Thoracic and Cardiovascular Surgery*, vol. 66, No. 3, Sep. 1973, pp. 350-360.

McGoon, M.D. et al., "Correction of the univentricular heart having two atrioventricular valves," *The Journal of Thoracic and Cardiovascular Surgery*, vol. 74, No. 2, Aug. 1977, pp. 218-226.

Lev, M.D., et al., "Single (Primitive) Ventricle," *Circulation*, vol. 39, May 1969, pp. 577-591.

Westaby with Basher, "Landmarks in Cardiac Surgery," 1997, pp. 198-199.

Shumacker, "Cardiac Aneurysms," *The Evolution of Cardiac Surgery*, 1992, pp. 159-165.

Feldt, M.D., "Current status of the septation procedure for univentricular heart," *The Journal of Thoracic and Cardiovascular Surgery*, vol. 82, No. 1, Jul. 1981, pp. 93-97.

Doty, M.D., "Septation of the univentricular heart,"*The Journal of Thoracic and Cardiovascular Surgery*, vol. 78, No. 3, Sep. 1979, pp. 423-430.

Carpentier et al., "Myocardial Substitution with a Stimulated Skeletal Muscle: First Successful Clinical Case," Letter to the Editor, p. 1267, Sep. 25, 1996.

Ianuzzo et al., "Preservation of the Latissimus Dorsi Muscle During Cardiomyoplasty Surgery," *J. Card. Surg.*, 1996:11:99-108.

Ianuzzo et al., "On Preconditioning of Skeletal Muscle: Application to Dynamic Cardiomyoplasty," Invited Commentary, *J. Card. Surg.*, 1996:11:109-110.

Chachques et al., "Latissimus Dorsi Dynamic Cardiomyoplasty," *Ann. Thorac. Surg.*, 1989:47:600-604.

Moreira et al., "Latissimus Dorsi Cardiomyoplasty in the Treatment of Patients with Dilated Cardiomyopathy," Supplement IV Circulation, Sep. 25, 1996, 7 pgs.

Lucas et al., "Long-Term Follow-Up (12 to 35 Weeks) After Dynamic Cardiomyoplasty," *JACC*, vol. 22, No. 3, Sep. 1993:758-67.

Batista et al., "Partial Left Ventriculectomy to Improve Left Ventricular Function in End-Stage Heart Disease," *J. Card. Surg.*, 1996:11:96-98.

"Congestive Heart Failure in the United States: A New Epidemic" Data Fact Sheet, National Heart, Lung, and Blood Institute, National Institutes of Health, Dec. 9, 1996, pp. 1-6.

Kormos et al., "Experience with Univentricular Support in Mortally III Cardiac Transplant Candidates," *Ann. Thorac. Surg.*, 1990:49:261-71.

Wampler et al., "Treatment of Cardiogenic Shock with the Hemopump Left Ventricular Assist Device," *Ann. Thorac. Surg.*, 1991:52:506-13.

McCarthy et al., "Clinical Experience with the Novacor Ventricular Assist System," *J. Thorac. Cardiovasc. Surg.*, 1991:102-578-87.

Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.

Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.

Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.

Bearnson et al., "Development of a Prototype Magnetically Suspended Rotor Ventricular Assist Device," *ASAIO Journal*, 1996, pp. 275-280.

Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372-375.

Medtronic, Inc. 1996 Annual Shareholders Report, 79 pages.

ABIOMED, Inc. Annual Report 1996, 32 pages.

Press Release dated Sep. 16, 1996, "ABIOMED Wins $8.5 Million Federal Contract to Qualify its Artificial Heart for Human Trials," 5 pages.

Press Release dated Sep. 26, 1996, ABIOMED's Temporary Artificial Heart System Reaches 200 U.S. Medical Center Milestone, 1 page.

Press Release dated May 17, 1996, "ABIOMED Receives FDA Approval to Expand Indications for Use of Cardiac Assist System," 1 page.

Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED" Wins NIH Grant to Develop Calcification-Resistant Plastic Heart Valve, 1 page.

Press Release dated Aug. 25, 1995, "ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS-5000 in More Than 100 U.S. Medical Centers," 1 page.

"Reversible Cardiomyopathy," *Thoratec's Heartbeat*, vol. 10.2, Aug. 1996, 4 pages.

Tsai et al., "Surface Modifying Additives for Improved Device-Blood Compatibility," *ASAIO Journal*, 1994, pp. 619-624.

Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.

Brochure entitled "Thoratec Ventricular Assist Device System—Because Heart Patients Come in All Sizes," date even with or prior to Jan. 2, 1997, 5 pages.

Press Release dated Oct. 3, 1994, "Heartmate System Becomes First Implantable Cardiac-Assist Device to be Approved for Commercial Sale in the U.S.," 2 pages.

Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.

Bach et al., "Early Improvement in Congestive Heart-Failure after Correction of Secondary Mitral Regurgitation in End-Stage Cardiomyopathy," *American Heart Journal*, Jun. 1995, pp. 1165-1170.

Schuler et al., "Temporal Response of Left Ventricular Performance to Mitral Valve Surgery," vol. 59, No. 6, Jun. 1979, pp. 1218-1231.

Huikuri, "Effect of Mitral Valve Replacement on Left Ventricular Function in Mitral Regurgitation," *Br. Heart J.*, vol. 49, 1983, pp. 328-333.

Pitarys II et al., "Long-Term Effects of Excision of the Mitral Apparatus on Global and Regional Ventricular Function in Humans," *JACC*, vol. 15, No. 3, Mar. 1, 1990, pp. 557-563.

Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404-406, Oct. 1987.

Savage, M.D., "Repair of left ventricular aneurysm," *The Journal of Thoracic and Cardiovascular Surgery*, vol. 104, No. 3, Sep. 1992, pp. 752-762.

Melvin, "Ventricular Radius Reduction Without Restriction: A Computational Analysis," *ASAIO Journal*, 45:160-165, 1999.

Cox, "Left Ventricular Aneurysms: Pathophysiologic Observations and Standard Resection," *Seminars in Thoracic and Cardiovascular Surgery*, vol. 9, No. 2, Apr. 1997, pp. 113-122.

Boyd et al., "Tricuspid Annuloplasty," *The Journal of Thoracic Cardiovascular Surgery*, vol. 68, No. 3, Sep. 1974, 8 pages.

"Heart 'jacket' could help stop heart failure progression," *Clinica*, 916, Jul. 10, 2000.

McCarthy et al., "Device Based Left Ventricular Shape Change Immediately Reduces Left Ventricular Volume and Increases Ejction Fraction in a Pacing Induced Cardiomyopathy Model in Dogs: A Pilot Study," *JACC*, Feb. 2000.

Acorn Cardiovascular, Inc. Abstracts, Nov. 13, 2000.

Acorn Cardiovascular Summary, undated, 1 page.

"Nation's First 'Heart Jacket' Surgery to Treat Heart Failure Performed at HUP; Novel 'Cardiac Support Device' Comes to America After Promising Results in Europe," Jun. 26, 2000, 3 pages.

Acorn Cardiovascular Company Overview, Jun. 2000, 6 pages.

Acorn Cardiovascular Company Overview, undated, 2 pages.
Acorn Cardiovascular Executive Summary, May 2000, 7 pages.
Acorn Cardiovascular Highlights, Abstracts, Mar. 10, 1999.
Acorn Cardiovascular Highlights, Abstracts, Apr. 19, 1999.
Acorn Cardiovascular Highlights, Abstracts, Oct. 1, 1999.
Acorn Cardiovascular Highlights, Abstracts, Nov. 9, 1999.
Batista, M.D. et al., "Partial Left Ventriculectomy to Treat End-Stage Heart Disease," *The Society of Thoracic Surgeons*, 1997, pp. 634-638.
Melvin, "Ventricular Radius-Reduction Without Resection, A Computational Assessment," 4 pages, undated.
Melvin et al., "Reduction of Ventricular Wall Tensile Stress by Geometric Remodeling Device," 1 page, undated.
Kay et al., "Surgical Treatment of Mitral Insufficiency", *The Journal of Thoracic Surgery*, 29: 618-620, 1955.
Harken et al., "The Surgical Correction of Mitral Insufficiency", *The Journal of Thoracic Surgery*, 28:604-627, 1954.
Bailey et al., "Closed Intracardiac Tactile Surgery", *Diseases of the Chest*, XXII:1-24, Jul. 1952.
Sakakibara, "A Surgical Approach to the Correction of Mitral Insufficiency", *Annals of Surgery*, 142:196-203, 1955.
Glenn et al., "The Surgical Treatment of Mitral Insufficiency: The Fate of A Vascularized Transchamber Intracardiac Graft", *Annals of Surgery*, 141:510-518, Apr. 1955.
Kay et al., "Surgical Treatment of Mitral Insufficiency", *Surgery*, 37:697-706, May 1955.
Bailey et al."The Surgical Correction of Mitral Insufficiency by the Use of Pericardial Grafts", *The Journal of Thoracic Surgery*, 28:551-603, Dec. 1954.
Harken et al., "The Surgical Correction of Mitral Insufficiency", *Surgical forum*, 4:4-7, 1953.
Melvin et al., "Reduction of Ventricular Wall Tensile Stress by Geometric Remodeling Device," 6 pages, 1999.
Shumacker, Jr., "Attempts to Control Mitral Regurgitation", *The Evolution of Cardiac Surgery*, 203-210, 1992.
P. McCarthy, Transcription of Mar. 13, 2000 Presentation at the American College of Cardiology, pp. 1-9.
English language Abstract of DE 19947885.
English language Abstract of DE 29619294.
US 6,197,052, 03/2001, Cosgrove et al. (withdrawn)

* cited by examiner

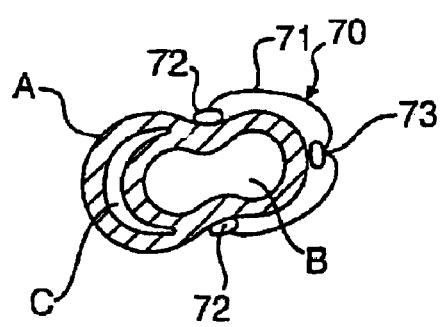
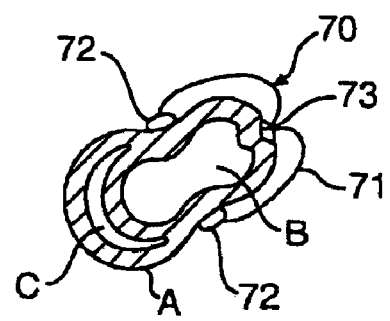
FIG. 10     FIG. 11

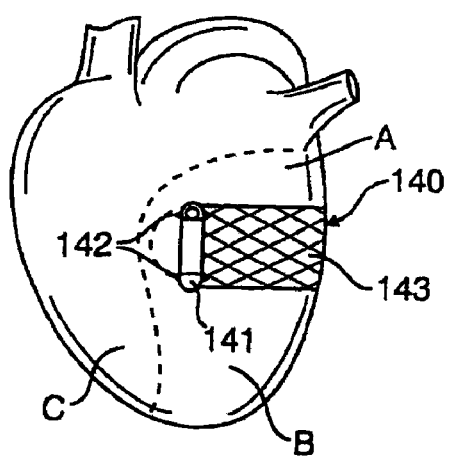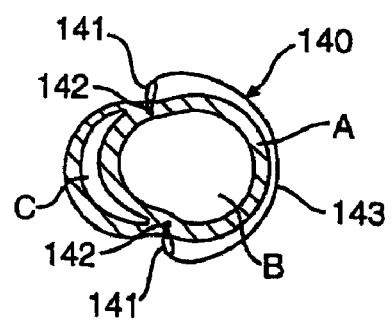
FIG. 16   FIG. 17

Fig. 33
Fig. 34
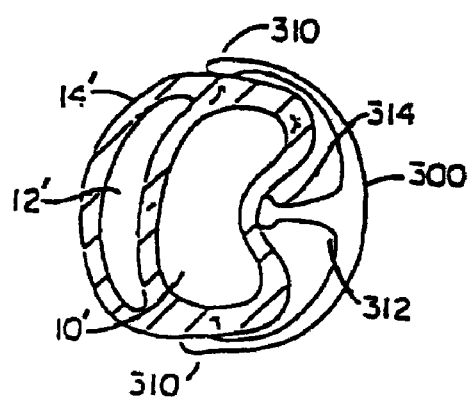
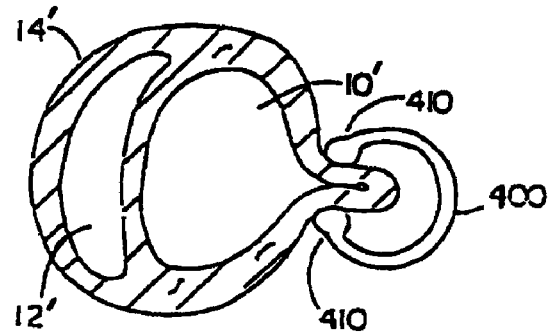

HEART WALL TENSION REDUCTION APPARATUS AND METHOD

RELATED APPLICATIONS

This application is a continuation of U.S. application Ser. No. 10/127,731 ("the '731 application") of Cyril J. SCHWEICH Jr. et al. for HEART WALL TENSION REDUCTION APPARATUS AND METHOD, filed on Apr. 23, 2002 now U.S. Pat. No. 7,883,539, which is a continuation-in-part of U.S. application Ser. No. 09/985,361 of Cyril J. SCHWEICH, Jr. et al. for HEART WALL TENSION REDUCTION APPARATUS AND METHOD, filed Nov. 2, 2001, now U.S. Pat. No. 6,589,160, which is a continuation of U.S. application Ser. No. 09/697,597, filed Oct. 27, 2000, now U.S. Pat. No. 6,332,864, which is a continuation of Application No. 09/492,777, filed Jan. 28, 2000, now U.S. Pat. No. 6,162,168, which is a continuation of Application No. 08/778,277, filed Jan. 2, 1997, now U.S. Pat. No. 6,050,936.

The '731 application also is a continuation-in-part of U.S. application Ser. No. 09/843,078 of Todd J. MORTIER et al. for STRESS REDUCTION APPARATUS AND METHOD, filed Apr. 27, 2001, now U.S. Pat. No. 6,402,680, which is a continuation of Application No. 09/522,068, filed Mar. 9, 2000, now U.S. Pat. No. 6,264,602, which is a continuation of Application No. 09/124,321, filed Jul. 29, 1998, now U.S. Pat. No. 6,077,214. The entirety of each of the above applications is incorporated herein by reference.

FIELD OF THE INVENTION

The present invention pertains to the field of apparatus for treatment of a failing heart. In particular, the apparatus of the present invention is directed toward reducing the wall stress in the failing heart.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior art treatments for heart failure fall into three generally categories. The first being pharmacological, for example, diuretics. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes like digoxin are cardiac glycosides and function to increase cardiac output by increasing the force and speed of cardiac muscle contraction. These drug therapies offer some beneficial effects but do not stop the progression of the disease.

Assist devices include mechanical pumps and electrical stimulators. Mechanical pumps reduce the load on the heart by performing all or part of the pumping function normally done by the heart. Currently, mechanical pumps are used to sustain the patient while a donor heart for transplantation becomes available for the patient. Electrical stimulation such as bi-ventricular pacing have been investigated for the treatment of patients with dilated cardiomyopathy.

There are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

SUMMARY OF THE INVENTION

The present invention pertains to a non-pharmacological, passive apparatus for the treatment of a failing heart. The device is configured to reduce the tension in the heart wall. It is believed to reverse, stop or slow the disease process of a failing heart as it reduces the energy consumption of the failing heart, decrease in isovolumetric contraction, increases sarcomere shortening during contraction and an increase in isotonic shortening in turn increases stroke volume. In embodiments, the device reduces wall tension during diastole (preload) and systole.

In an embodiment, the apparatus includes a compression member for drawing at least two walls of a heart chamber toward each other to reduce the radius or area of the heart chamber in at least one cross sectional plane. In one embodiment of the apparatus, a frame is provided for supporting the compression member.

Yet another embodiment of the invention includes a damp having two ends biased toward one another for drawing at least two walls of a heart chamber toward each other. The damp includes at least two ends having atraumatic anchoring member disposed thereon for engagement with the heart or chamber wall.

The present invention also pertains to a device and method for reducing mechanical heart wall muscle stress. Heart muscle stress is a stimulus for the initiation and progressive enlargement of the left ventricle in heart failure. Reduction of heart wall stress with the devices and methods disclosed herein is anticipated to substantially slow, stop or reverse the heart failure disease process. Although the primary focus of the discussion of the devices and methods of the present invention herein relates to heart failure and the left ventricle, these devices and method could be used to reduce stress in the hearts other chambers.

The devices and methods of the present invention can reduce heart wall stress throughout the cardiac cycle including end diastole and end systole. Alternatively, they can be used to reduce wall stress during the portions of the cardiac cycle not including end systole. Those devices which operate throughout the cardiac cycle are referred to herein as "full cycle splints". Those devices which do not operate to reduce wall stress during end stage systole are referred to as "restrictive devices". Restrictive devices include both "restrictive splints" which alter the geometric shape of the left ventricle, and "wraps" which merely limit the magnitude of the expansion of the left ventricle during diastolic filling without a substantial shape change.

While it is desirable to reduce wall stress for the treatment of heart failure, to slow or reverse the disease process and to increase heart wall muscle shortening and pumping efficiency, it is also desirable to maintain or improve stroke volume and allow for variable preload.

Improving muscle shortening both total length change and extent at end systole, is particularly important in symptomatic heart failure wherein the heart has decreased left ventricle function and has enlarged. Full cycle splinting can be used to obtain a substantial increase in muscle shortening. Improved shortening will lead to an increase in pump function, and chronically may result in muscle strengthening and reversal of the disease because of increased pumping efficiency. The increase in shortening should be balanced against a reduction in chamber volume.

In asymptomatic, early stage heart failure, it may be possible to use only a restrictive device or method as elevated wall stress is considered to be an initiator of muscle damage and chamber enlargement. Restrictive devices and methods acting during diastole will reduce the maximum wall stress experienced during end diastole and early systole. It should be understood that restrictive devices and methods can be used in combination with full cycle splinting to more precisely control or manipulate stress reduction throughout the cardiac cycle.

BRIEF DESCRIPTION OF THE DRAWINGS

FIG. 10 is a horizontal cross section of a heart including a splint having full cycle and restrictive elements at the beginning of diastolic filling;

FIG. 11 is a view of the splint of FIG. 10 at end diastole;

FIG. 16 is a vertical view of a heart including a partial circumferential strap;

FIG. 17 is a horizontal cross sectional view of the heart and strap of FIG. 16;

FIG. 33 is a transverse cross-section of the left and right ventricles of a human heart showing the placement of an external compression frame structure in accordance with the present invention;

FIG. 34 is a transverse cross-section of the left and right ventricles of a human heart showing a clamp in accordance with the present invention;

DESCRIPTION OF THE EMBODIMENTS

Figure 1:
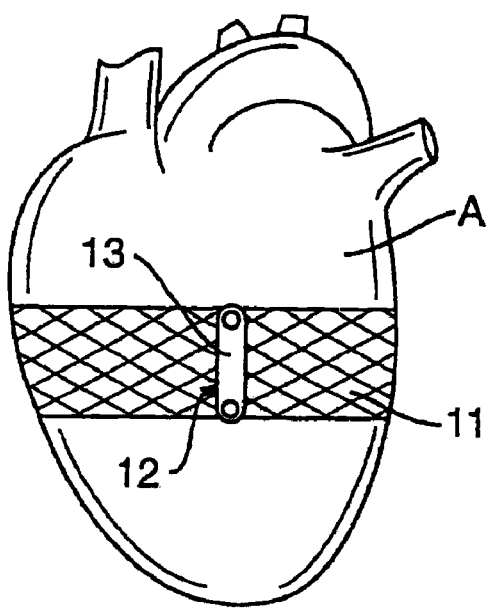
FIG. 1 is a vertical side view of a heart including a transventricular splint and band splint.

The present invention is directed at reducing wall stress in a failing heart. Diastolic wall stress is considered to be an initiator of muscle damage and chamber enlargement. For this reason, it is desirable to reduce diastolic wall stress to prevent the progression of the disease. The significant impact of stress occurs at all stages and functional levels of heart failure, however, independent of the original causes. For example, in asymptomatic early stages of heart failure, mechanical stress can lead to symptomatic heart failure marked by an enlarged heart with decreased left ventricle function. As the heart enlarges, mechanical stress on the heart wall increases proportionally to the increasing radius of the heart in accordance with LaPlace's Law. It can thus be appreciated that as stress increases in symptomatic heart failure, those factors that contributed to increasing stress also increase. Thus, the progression of the disease accelerates to late stage heart failure, end stage heart failure and death unless the disease is treated.

Three parameters influence mechanical stress on the muscle. These are: (1) muscle mass, i.e., as reflected by the thickness of the muscle; (2) pressure in the chamber which is a function of the resistance to blood flow of the patient's vasculature and the volume of blood within the patient; and (3) chamber geometry. The present invention pertains to devices and methods for directly and passively changing chamber geometry to lower wall stress. In addition to treatment of heart failure, the devices and methods of the present invention also lend themselves to application in the case of a decrease in cardiac function caused by, for example, acute myocardial infarction.

The devices disclosed herein for changing chamber geometry are referred to as "splints". In addition to splints, wraps which can be placed around the heart can limit muscle stress without the chamber shape change. When a wrap is used, wall stress is merely transferred to the wrap, while the generally globular shape of the heart is maintained. A wrap could be used in conjunction with a splint to modulate heart wall stress reduction at various stages of the cardiac cycle.

The present invention includes a number of splint embodiments. Splints and wraps can be classified by where in the cardiac cycle they engage the heart wall, i.e., mechanically limit the size of the left ventricle in the case of wraps and change the geometry of the ventricle in the case of splints. If a splint or wrap only begins to engage during diastolic filling, the splint can be termed a "restrictive splint". If the splint or wrap is engaged throughout the cardiac cycle, both during diastolic filling and systolic contraction and ejection, the splint can be termed a "full cycle splint". The wrap will generally be a restrictive device which begins to engage during diastolic filling to increase the elastance (reduces compliance) of the chamber. If a wrap is made from elastic material it may engage full cycle, but the force required to elongate the wrap will increase as diastolic filling progresses, preload strain will be reduced without an improvement in systolic contraction.

Figure 2:
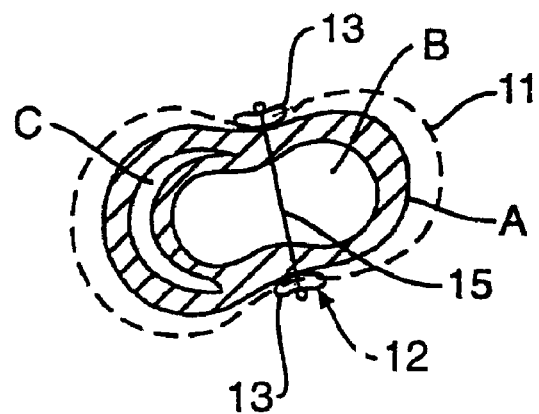
FIG. 2 is a horizontal cross section of the heart, splint and band splint of FIG. 1.

FIG. 1 is a view of a heart A in a normal, generally vertical orientation. A wrap 11 surrounds heart A and a transventricular splint 12 extends through the heart and includes an anchor or anchor pad 13 disposed on opposite sides of the heart. FIG. 2 is a horizontal cross sectional view of heart A taken through wrap 11 and splint 12. Splint 12 includes a tension member 15 extending through left ventricle B. Anchor pads 13 are disposed at each end of tension member 15. Right ventricle C is to the left of left ventricle B.

In FIG. 1, wrap 11 and splint 12 are shown engaged with heart A. In FIG. 2, heart A is shown spaced from wrap 11 except at anchor pads 13. In FIG. 2, heart A is thus at a point in the cardiac cycle where the muscles are shortening during systole, or have yet to stretch sufficiently during diastolic expansion to reach wrap 11. Accordingly, wrap 11 can be considered a restrictive device as it does not engage the heart full cycle. Although wrap 11 is in contact with heart A at pads 13, only the splint is providing a compressive force to change the shape of the heart and limiting the stress of the heart in FIG. 2.

If heart A, as shown in FIG. 2 is at end systole, transventricular splint 12 is a full cycle device as the cross section of left ventricle B does not have the generally circular unsplinted shape. Alternately, wrap 11 could be secured to heart A by sutures or other means than splint 12, in which case wrap 11 would be merely a restrictive device. It should be noted that unless wrap 11 extends vertically along heart A a sufficient amount, as heart A expands and engages wrap 11, the portion of left ventricle B disposed above or below wrap 11 could expand substantially further than that portion of the left ventricle wall restrained by wrap 11. In such a case, left ventricle B could have a bi-lobed shape in a vertical cross section. As such, the wrap 11 would not be merely limiting the size of the left ventricle, but rather inducing a shape change in the left ventricle. In such a case, the element 11 would not be a wrap, but rather a splint which could be referred to as a "band splint".

Each of the splints, wraps and other devices disclosed in this application preferably do not substantially deform during the cardiac cycle such that the magnitude of the resistance to the expansion or contraction of the heart provided by these devices is reduced by substantial deflection. It is, however, contemplated that devices which deflect or elongate elastically under load are within the scope of the present invention, though not preferred. The materials from which each device are formed must be biocompatible and are preferably configured to be substantially atraumatic.

Figure 3:
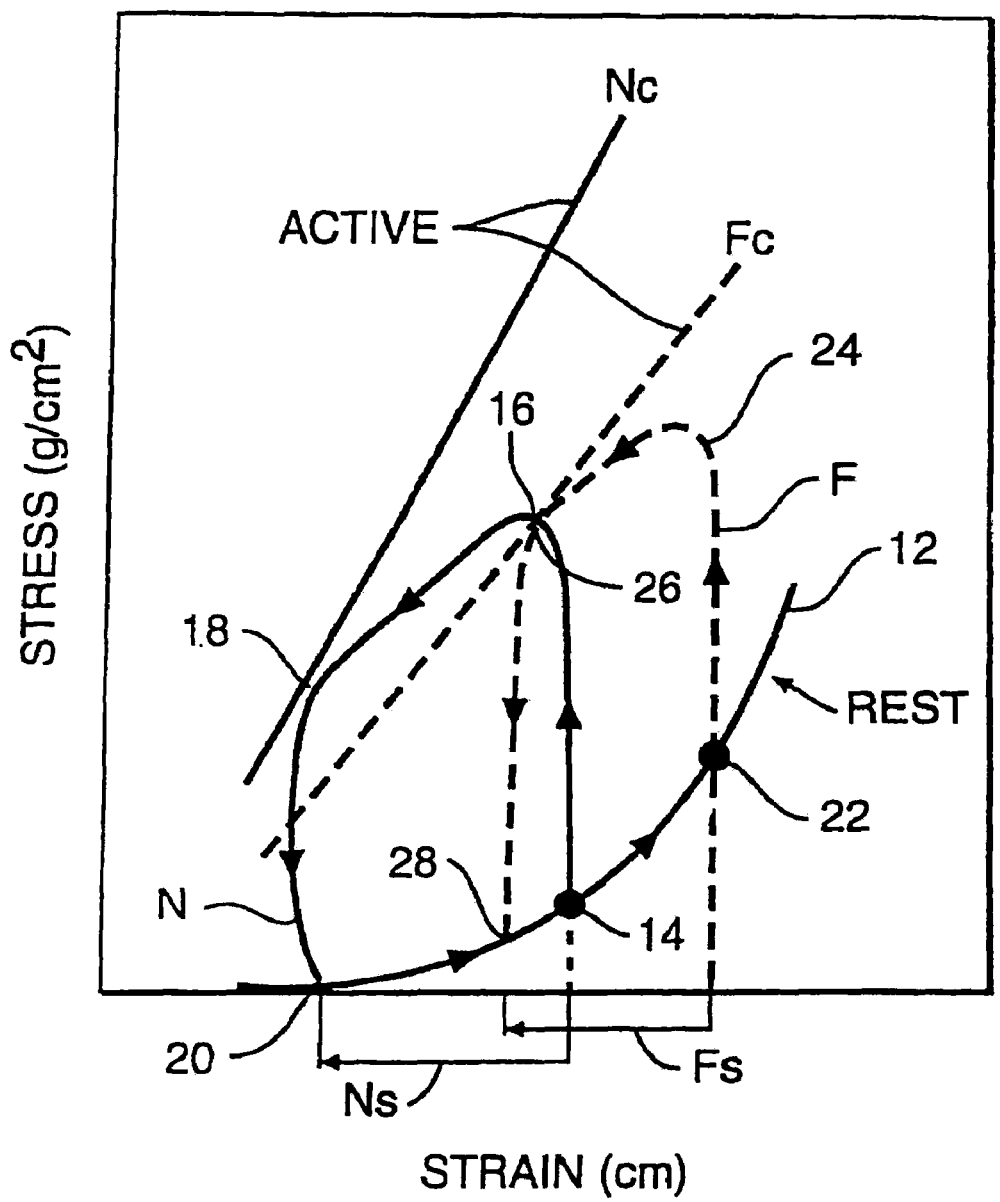
FIG. 3 is a graph showing the relationship between stress and strain for the sarcomeres of the left ventricle for a normal and failing heart throughout the cardiac cycle.

The distinction between restrictive devices, such as restrictive splints and wraps, and full cycle splints and wraps, can be better understood by reference to FIG. 3. FIG. 3 is a plot of sarcomere, i.e., heart wall muscle, stress in (g/cm$^2$) versus strain throughout a normal cardiac cycle N, and a failing heart cardiac cycle F. The cardiac cycles or loops shown on FIG. 3 are bounded by the normal contractility curve $N_c$ and failing heart contractility curve $F_c$ above and to the left, and the diastolic filling curve 12 toward the bottom and right. Contractility is a measure of muscle stress at an attainable systolic stress at a given elongation or strain. It can be appreciated that the muscle contractility $N_c$ of normal muscle tissue is greater than the contractility $F_c$ of the muscle tissue of a failing heart.

The diastolic filling curve 12 is a plot of the stress in the muscle tissue at a given elongation or strain when the muscle is at rest.

An arbitrary beginning of the normal cardiac cycle N can be chosen at end diastole 14, where the left ventricle is full, the aortic valve is closed. Just after end diastole 14, systole begins, the sarcomere muscles become active and the mitral valve closes, increasing muscle stress without substantially shortening (sometimes referred to as "isovolumic contraction"). Stress increases until the aortic valve opens at 16. Isotonic shortening begins and stress decreases and the muscles shorten until end systole 18, where the blood has been ejected from the left ventricle and the aortic valve closes. After end systole 18, diastole begins, the muscles relax without elongating until diastolic filling begins when the mitral valve opens at 20. The muscles then elongate while the mitral valve remains open during diastolic filling until end diastole 14. The total muscle shortening and lengthening during the normal cycle N is $N_S$.

An analogous cycle F also occurs in a failing heart. As the left ventricle has dilated, in accordance with LaPlace's Law, the larger radius of a dilated left ventricle causes stress to increase at a given blood pressure. Consequently, a failing heart must compensate to maintain the blood pressure. The compensation for the increased stress is reflected in the shift to the right of failing heart cardiac cycle F relative to the normal cycle N. The stress at end diastole 22 is elevated over the stress at end diastole 14 of the normal heart. A similar increase can be seen for the point at which the aortic valve opens 24, end systole 26 and the beginning of diastolic filling 28 relative to the analogous points for the normal cycle N. Muscle shortening and elongation $F_S$ throughout the cycle is also reduced in view of the relative steepening of the diastolic curve 12 to the right and the flatter contractility curve $F_c$ relative to the normal contractility $N_c$.

By reference to the heart cycle stress strain graph of FIG. 3, the effect on mechanical muscle stress and strain caused by the use of the devices and methods of the present invention can be illustrated. Restrictive devices begin to engage during diastolic filling, which in the case of a failing heart occurs along diastolic filling curve 12 between point 28 and 22. Restrictive devices do not engage at end systole 26. Thus, the acute effect of placement of a restrictive device is to reduce muscle stress at end diastole relative to the stress at point 22, and shift the line 22-24 to the left reducing muscle shortening and elongation $F_S$. Acutely, the cardiac cycle will still operate between the failing heart contractility curve $F_c$ and the diastolic filling curve 12. If chronic muscle contractility increases such that the muscle contractility curve $F_c$ shifts back toward the normal heart contractility curve $N_C$ as a consequence of the stress reduction, the stress/strain curve F of the cardiac cycle will shift to the left reducing mechanical stress still further.

The effect on the stress/strain relationship of a full cycle splint will acutely shift the entire stress/strain curve F for the cycle to the left. That is, stress is reduced at both end diastole 22 and end systole 26. Muscle shortening and elongation $F_s$ will increase acutely. If, as in the case of a restrictive splint, muscle contractility $F_C$ improves, the entire cardiac cycle curve F will shift further to the left reducing mechanical stress still further.

The type and magnitude of shape change are important factors in determining the effectiveness of splinting. There are several types of lower stress cardiac geometries that can be created from an enlarged globular left ventricular chamber typically associate with heart failure. They include lobed, disc-like, narrowed elongate, and multiple vertically stacked bulbs.

Figure 4:
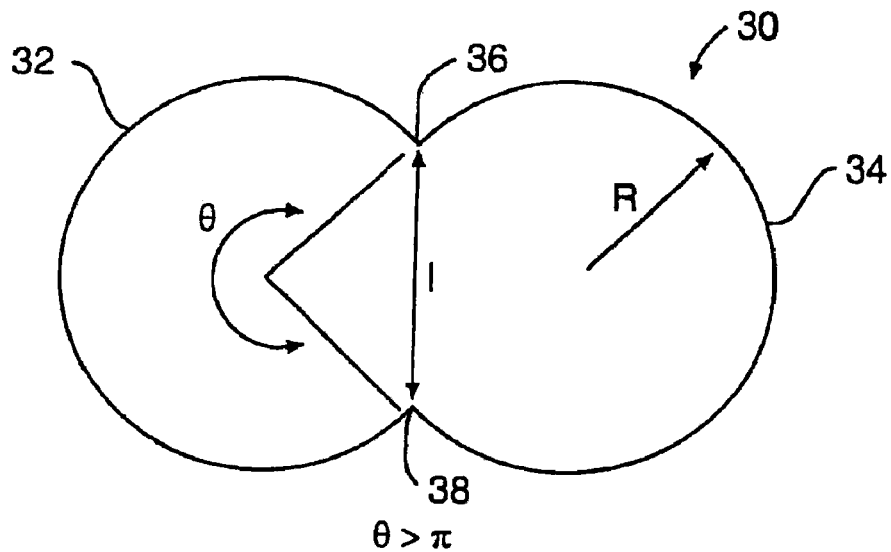
FIG. 4 is an idealized horizontal cross section of a left ventricle splinted to form two lobes.

FIG. 4 shows an idealized horizontal cross section of a left ventricle 30 subdivided into two symmetrical lobes 32 and 34 having an arc passing through an angle $\theta > \pi$, and a radius R. Lobes 32 and 34 can be formed using a splint, such as transventricular splint 12 shown in FIGS. 1 and 2. Lobes 32 and 34 are joined at points 36 and 38. Points 36 and 38 are separated by a distance l.

Figure 5:
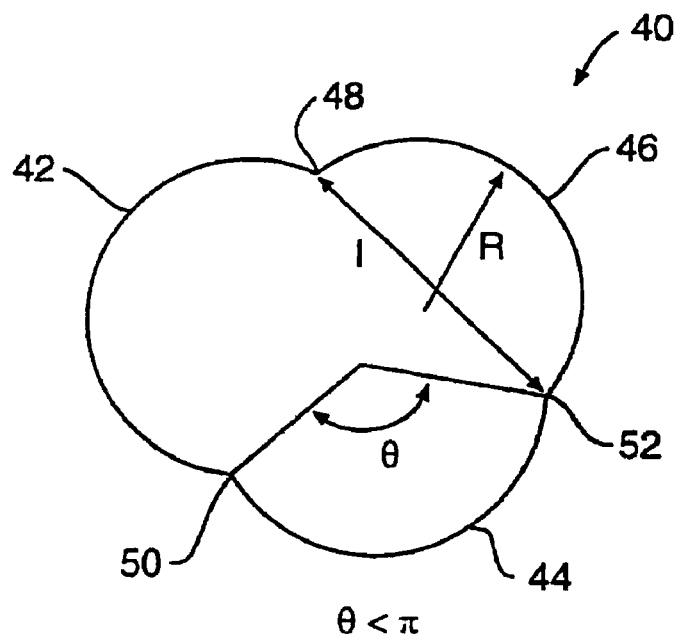
FIG. 5 is an idealized horizontal cross sectional left ventricle splinted to form three lobes.

FIG. 5 is an idealized horizontal cross section of a left ventricle 40 subdivided into three generally equal sized lobes 42, 44 and 46. Each lobe has an equal radius and has an arc passing through an angle less than $\pi$. Adjacent ends of the lobes 48, 50 and 52 are separated by a distance l. A plurality of transventricular splints such as splint 12 as shown in FIGS. 1 and 2 could be extended between adjacent ends 48, 50 and 52 to form lobe's 42, 44 and 46.

For a restrictive splint, the horizontal cross sections 30 and 40 will have a generally circular shape, i.e., a non-splinted shape at end systole. As diastolic filling proceeds, the radius of the circular shape will continue to increase until the splint engages. At the point the splint engages, the lobed shape will begin to form. In the case of the two lobe splinting of FIG. 4, the radius will continue to increase as diastolic filling proceeds. In the case of the three or more lobed shape, such as the three lobed configuration of FIG. 5, radius R will decrease as diastolic filling proceeds. The radius will continue to decrease unless or until the pressure in the heart causes the heart to expand such that the arc of the lobe passes through an angle $\theta$ greater than $\pi$.

In the case of a full cycle splint, at end systole, the splint will already be engaged. Thus, for a full cycle splint at end systole, the horizontal cross section of the chamber will not have the normal generally circular shape. Rather, at end systole, the horizontal cross sections 30 and 40 will have a lobed shape such as shown in FIGS. 4 and 5. Subsequent shape change during diastolic filling for a full cycle splint will be similar to that described with respect to restrictive splints.

In view of LaPlace's Law which states that stress is directly proportional to radius of curvature, it can be appreciated that whether the radius is increasing or decreasing during diastolic filling, will have an impact on heart pumping performance. Where R is increasing during diastolic filling, wall stress will increase more rapidly than where R is decreasing. The number of lobes that are created can significantly influence the level of end diastolic muscle stress reduction achieved through splinting. Eventually adding additional lobes forms a configuration which approaches a behavior similar to a wrap. If a wrap is substantially inelastic, or of sufficient size, a wrap will only engage the heart wall at some stage of diastolic filling. If the wrap is substantially inelastic, as pressure increases in the chamber during diastolic filling, stress in the heart wall muscle will increase until the wrap fully engages and substantially all additional muscle elongating load created by increased chamber pressure will be shifted to the wrap. No further elongation of the chamber muscles disposed in a horizontal cross section through the wrap and the chamber will occur. Thus, inelastic wraps will halt additional preload muscle strain (end diastolic muscle stretch).

The type of shape change illustrated in FIGS. 4 and 5 is of substantial significance for restrictive splints. It is undesirable in the case of restrictive splints, to excessively limit preload muscle strain. The Frank-Starling Curve demonstrates the dependence and need for variable preload muscle strain on overall heart pumping performance. During a person's normal activities, their body may need increased blood perfusion, for example, during exertion. In response to increased blood perfusion through a person's tissue, the heart will compensate for the additional demand by increasing stroke volume and/or heart rate. When stroke volume is increased, the patient's normal preload strain is also increased. That is, the lines 14-16 and 22-24 of the normal and failing hearts, respectively, will shift to the right. An inelastic wrap will, at engagement, substantially stop this shift. In the case of the bi-lobed shape change of FIG. 4 or a multiple lobed change having a small number of lobes of FIG. 5, significant stress reduction can be achieved while allowing for variable preload strain. If the number of lobes is increased substantially, however, variable preload will decrease as the multi-lobed configuration approaches the performance of an inelastic wrap.

The magnitude of shape change in the case of full cycle splinting becomes very important as full cycle splinting generally reduces chamber volume more than restrictive splinting. Although as with restrictive devices, the type of shape change is also important to allow for variable preload strain. Both restrictive device and full cycle splints reduce chamber volume as they reduce the cross sectional area of the chamber during the cardiac cycle. The magnitude of the shape change can vary from very slight at end diastole, such that chamber volume is only slightly reduced from the unsplinted end diastolic volume, to an extreme reduction in volume, for example, complete bifurcation by transventricular splint. The magnitude of the shape change, for example, as measured by the ratio of splint length to non-splinted ventricular diameter, is preferably modulated to reduce muscle stress while not overly reducing chamber volume. For full cycle splint, the reduction of chamber volume is compensated for by increased contractile shortening, which in turn leads to an increased ejection fraction, i.e., the ratio of the stroke volume to chamber volume. For given stress/volume and stress/shortening relationships, there will be a theoretical optimum maximal stroke volume. Clinically, 20% to 30% stress reduction is expected to be attainable through full cycle bi-lobe splinting. See U.S. Pat. No. 5,961,440 and the discussion further herein for calculation of stress reduction for idealized bi-lobe splinting.

When using the full cycle and restrictive devices described herein, caution should be exercised to limit the pressure on the coronary vasculature. In the case of transventricular splints, valve structure, electrical pathways and coronary vasculature should be avoided.

Figure 6:
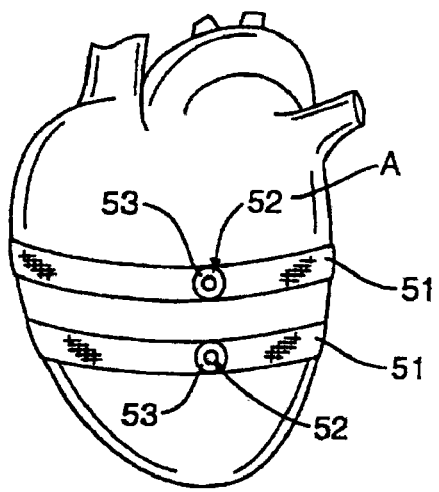
FIG. 6 is a vertical view of a heart including two transventricular splints and two band splints.
Figure 7:
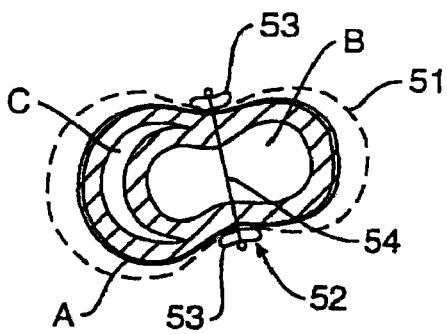
FIG. 7 is a cross sectional view of the heart, a band splint and a splint of FIG. 6.

FIG. 6 is a vertical view of a heart A similar to that shown in FIG. 1. Rather than having a single band splint surrounding heart A, there are two band splints 51 affixed to the heart by two transventricular splints 52. Splints 52 include oppositely disposed anchors or anchor pads 53. FIG. 7 is a horizontal cross sectional view of heart A of FIG. 6, wraps 51 and splint 52. Splints 52 include a tension member 54 disposed through left ventricle B. Pads 53 are disposed on the opposite ends of tension members 54. Right ventricle C is shown to the left of left ventricle B.

Splints 52 can be restrictive or full cycle splints. Band Splints 51 are shown as restrictive band splints as in FIG. 6, heart A is shown engaged with the band splints 51, whereas in FIG. 7, heart A has contracted to move away from band splints 51. Wraps 51 and splints 52 should be made from biocompatible materials. Band splints 51 are preferably made from a pliable fabric or other material which resists elongation under normal operating loads. Band splints 51 can, however, be made from an elastic material which elongates during the cardiac cycle. Tension members 54 also preferably resist elongation under normal operating loads. Tension members 54 can, however, be made from an elastic material which elongates during the cardiac cycle.

Figure 8:
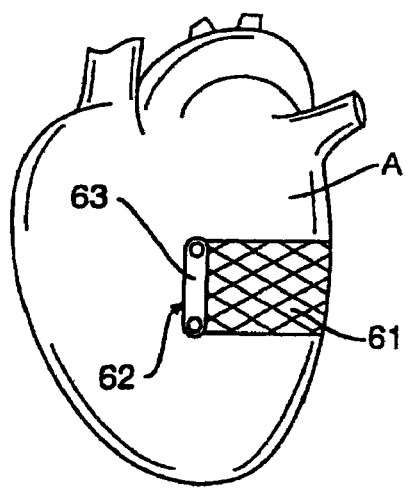
FIG. 8 is a vertical view of a heart including a transventricular splint and a partial band splint.
Figure 9:
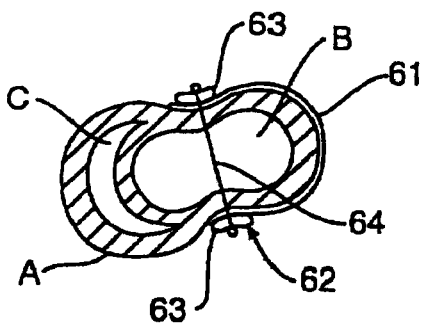
FIG. 9 is a horizontal cross sectional view of the heart, splint and band splint of FIG. 8.

FIG. 8 is a vertical view of heart A, partial wrap 61 and transventricular splint 62. Transventricular splint 62 includes anchor pads 63. FIG. 9 is a horizontal cross sectional view of heart A, partial band splint 61 and splint 62. Splint 62 is essentially similar to wrap or band splint 12 shown in FIGS. 1 and 2. Partial band splint 61 is also essentially similar to wrap or band splint 11 shown in FIGS. 1 and 2 except that band splint 61 only surrounds a portion of heart A. This portion is shown in FIGS. 8 and 9 to the left including a portion of left ventricle B.

FIG. 10 is a horizontal cross sectional view of left ventricle B and right ventricle C of heart A taken at a similar elevation as that shown in FIG. 2. A splint 70 is shown disposed on heart A. Splint 70 includes a frame having two heart engaging anchors or pads 72 disposed at its opposite ends. A third heart engaging pad 73 is disposed along frame 70 approximately midway between pads 72.

Pads 72 are shown engaged with heart A to change the shape of ventricle B in FIG. 10. Pads 73 are not engaged with heart A in FIG. 10. FIG. 11 is the same horizontal cross sectional view as FIG. 10 except that heart A has to contact pad 73 to create a further shape change of left ventricle B.

Frame 70 is preferably rigid enough that pads 72 could be disposed on the heart for full cycle splinting and sufficiently adjustable that pads 72 could be spaced further apart for restrictive splinting. Pad 73 accomplishes restrictive splinting. Frame 71, pads 72 and 73 of splint 70 are made of a biocompatible material. Pads 72 and 73 are preferably substantially atraumatic.

Figure 12:
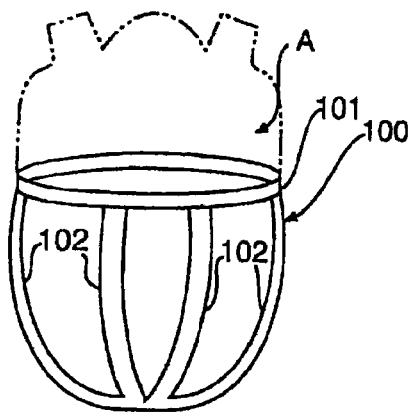
FIG. 12 is a vertical view of the heart in phantom line including a band splint.

FIG. 12 is a vertical view of heart A shown in phantom line. Shown disposed about the ventricles of heart A is a basket-like band splint 100. Band splint 100 includes a horizontal encircling band 101 around an upper region of the ventricles and four bands 102 which extend downward toward the apex of heart A. It can be appreciated that bands 102 can act as splints to form four lobes in heart A in a horizontal plane. Depending on the placement of bands 102 around heart A, lobes could be created only in the left ventricle or in the left ventricle and/or other chambers of the heart. Band 102 is joined at the apex. Band 101 and band 102 can be made from a webbing, fabric or other biocompatible material.

If band splint 100 substantially elongated elastically under normal operating loads, it could be friction fit to heart A and act full cycle, limiting muscle stress at end diastole as well end systole. Band splint 100 could be sutured into place or otherwise held on heart A and act as a restrictive device. If band 101 were securely fastened to heart A, bands 102 could limit the vertical elongation of heart A during diastolic filling.

Figure 13:
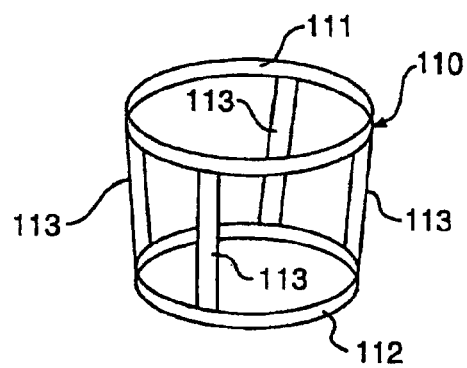
FIG. 13 is an alternate embodiment of the band splint of FIG. 12.

FIG. 13 is an alternate embodiment 110 of the band splint of FIG. 12. Band splint 110 includes a horizontally heart encircling band 111 and four bands 113 extending downward from band 111. Bands 113, however, unlike bands 102 of band splint 100 do not extend to the apex of heart A, but rather to a second horizontally heart encircling band 112.

Band splint 110 could be made of the same materials as band splint 100. Band splint 110 can also be used in a manner similar to band splint 100 except that band splint 110 would limit the vertical elongation of the ventricles less than band splint 100.

Figure 14:
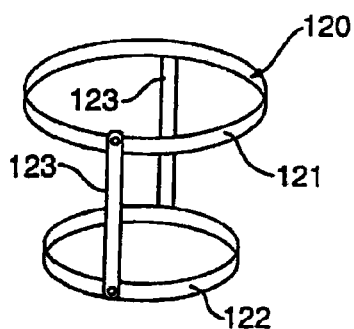
FIG. 14 is an alternate embodiment of the band splint of FIG. 12.

FIG. 14 is yet another alternate embodiment 120 of the wrap of FIG. 12. Band splint 120 closely resembles alternate embodiment 110 of FIG. 13, except that rather than having four vertically extending web members, band splint 120 includes two substantially rigid members 123 interconnecting two horizontally encircling web members 121 and 122.

Figure 15:
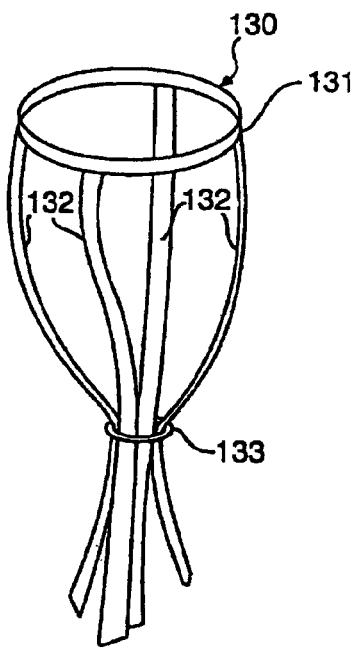
FIG. 15 is an alternate embodiment of the band splint of FIG. 12.

FIG. 15 is yet another alternate embodiment 130 of the band splint of FIG. 12. Like the wrap of FIG. 12, band splint 130 includes a horizontally encircling member 131 and four downwardly extending members 132. At a location proximate of the apex of heart A, members 132 are joined by a ring 133. Members 132 extend through ring 133. Ring 133 can be used to adjust the length of members 132 between band 131 and ring 133. Ring 133 can be formed from metallic material and crimped inwardly to fix its position along members 132. Other means of holding ring 133 in position would be readily apparent to those skilled in the art.

FIG. 16 is a vertical view of heart A including a partial band splint 140 secured around a substantial portion of left ventricle B. Band splint 140 includes a vertically elongating anchor member 141 which sutures 142 can encircle to anchor member 141 to heart A. A band 143 extends generally horizontally from anchor member 141 to an opposite anchor 141.

The length of band 143 can be seen in its entirety in FIG. 17 which is a horizontal cross sectional view of heart A through band 143, left ventricle B and right ventricle C. In FIG. 16, heart A is shown engaged with band 143, however, in FIG. 17, band 143 is shown spaced from heart A. Thus, in this configuration, wrap 140 would be acting as a restrictive device. If band splint 140 were made from a material that substantially deforms elastically under normal loads, band splint 140 could also be secured sufficiently snuggly to heart A to act as a full cycle device. Preferably, however, band 143 of band splint 140 is formed from a webbing or substantially inelastic fabric.

Figure 18:
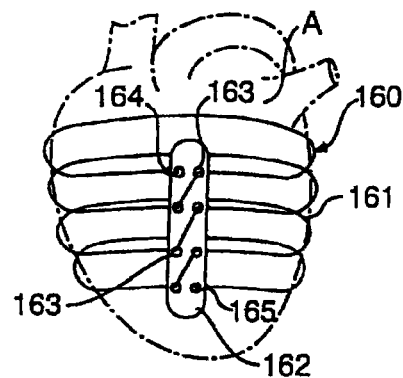
FIG. 18 is a vertical view of a heart in phantom line including a single element wrap including longitudinal axis securing points.

FIG. 18 is a vertical view of heart A including a wrap 160. Wrap 160 can include a single thread or line 161 encircling the heart several times. After line 161 encircles heart A, line 161 can be threaded through a bar 162, including a plurality of eyelets 163 spaced along its length in pairs. Bar 162 is preferably rigid enough to substantially maintain the distance between eyelets 163 under normal operating loads.

When line 161 is placed in heart A, one end of line 161 can be tied to bar 162 at 164. Line 161 can then encircle the heart and be drawn through eyelet 162 adjacent the beginning of line 161 at 164. Line 161 can then be drawn through one eyelet 163 of a lower pair of eyelets to encircle the heart again. This process continues until line 161 is tied to an eyelet 163 at 165. It can be appreciated that wrap 160 could be used as a restrictive or full cycle device depending on the diameter of loop formed by line 161.

Figure 19:
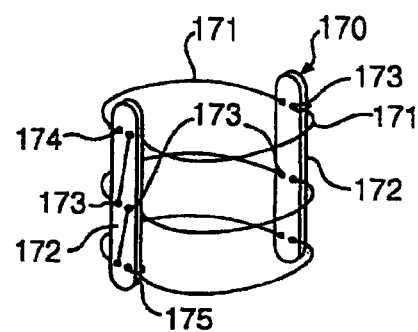
FIG. 19 is an alternate embodiment of the wrap of FIG. 18.

FIG. 19 is an alternate embodiment 170 of the wrap of FIG. 18. Wrap 170, however, includes two vertically extending bars 172 having eyelets 173 through which line 171 is threaded. Line 171 can be tied to one of the bars 172 at 174 and 175.

Figure 20:
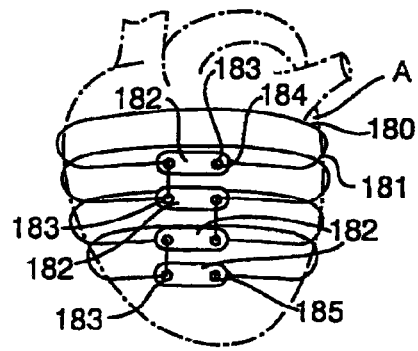
FIG. 20 is an alternate embodiment of the wrap of FIG. 18.

FIG. 20 is a vertical view of heart A including yet another embodiment 180 of the wrap of FIG. 18. Wrap 180 includes a line 181 encircling heart A a plurality of times. Rather than having a single vertically extending bar 162 to position line 180 on heart A, wrap 180 includes a plurality of horizontal bars 182 including a pair of eyelets 183. One end of line 181 is tied to an upper bar 182 at 184 and the opposite end of line 181 is tied to a lower bar 182 at 185. Between 184 and 185, line 181 is threaded through eyelets 182 to form the heart encircling pattern shown in FIG. 20.

Figure 21:
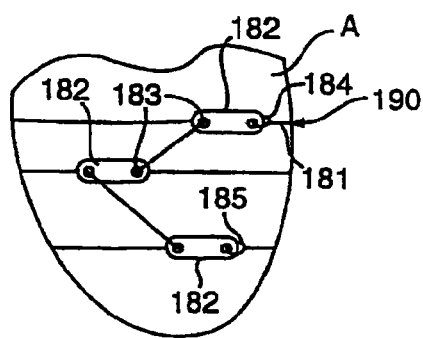
FIG. 21 is an alternate embodiment of the wrap of FIG. 18.

FIG. 21 is a vertical view of heart A including yet another alternate embodiment 190 of the wrap of FIG. 18. Wrap 190 closely resembles 180 of FIG. 20. Line 181 has, however, been threaded through eyelets 183 of bars 182 in a pattern which, unlike that of FIG. 20, bars 182 are disposed at various selected locations around the circumference of heart A.

Figure 22:
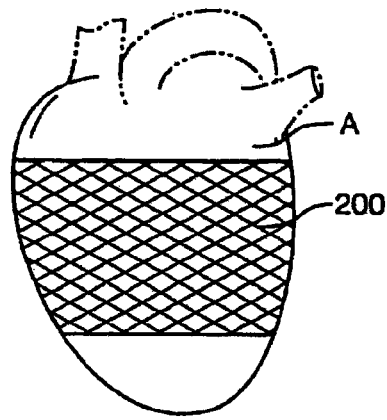
FIG. 22 is a vertical view of the heart including a mesh wrap.

FIG. 22 is a vertical view of heart A including a wrap 200. Wrap 200 is substantially similar to wrap 11 of FIGS. 1 and 2, except that wrap 200 extends vertically a greater distance than wrap 11. Wrap 200 is not shown with a transventricular splint. It can be appreciated that wrap 200 could be used as restrictive or full cycle device.

Figure 23:
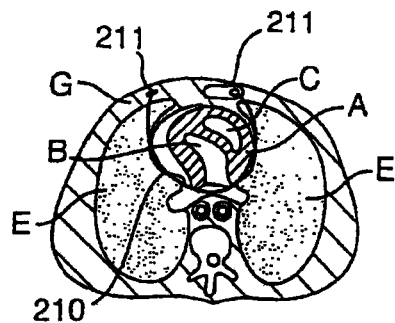
FIG. 23 is a cross sectional view of a patient's torso and heart showing a band splint anchored to the patients ribs.
Figure 24:
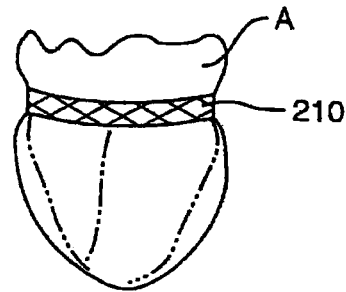
FIG. 24 is a partial vertical view of the heart and band splint of FIG. 23.

FIG. 23 is a horizontal cross section of a human torso including heart A, left ventricle B, right ventricle C, lungs E and ribs G. A wrap 210 is shown partially encircling heart A. Opposite ends of wrap 210 are anchored at 211 to ribs G. At 211, wrap 210 can be anchored to ribs G by bone screw, knot or other means of fastening. It can be appreciated that band splint 210 could be used as a restrictive or full cycle device.

Figure 25:
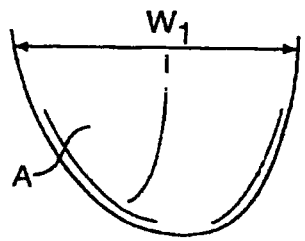
FIG. 25 is a partial vertical view of a failing heart.
Figure 26:
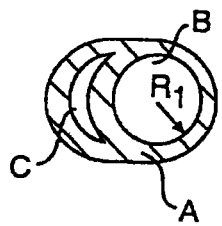
FIG. 26 is a cross sectional view of the heart of FIG. 25.

FIG. 25 is a vertical view of heart A having a horizontal width $W_1$. FIG. 26 is an idealized horizontal cross sectional view of heart A of FIG. 25. Heart A includes left ventricle B and right ventricle C. Left ventricle B has a radius $R_1$.

Figure 27:
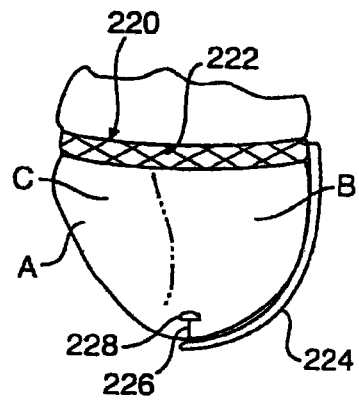
FIG. 27 is a vertical view of the heart for decreasing the horizontal radius of the ventricles and increasing their vertical length.

FIG. 27 is a view of a device 220. Device 220 includes a horizontally encircling band 222 which can be affixed to heart A by sutures, other attachment means or friction fit. Extending from band 222 is a substantially rigid elongate member 224. Member 224 extends to the apex of heart A. Pin 226 extends into left ventricle B of the apex. An anchor or pad 228 is disposed within left ventricle B to anchor the apex of heart A to elongate member 224. Elongate member 224 can be made of sufficient length such that heart A is vertically elongate full cycle, or alternately not at end diastole.

Figure 28:
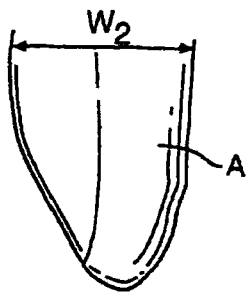
FIG. 28 is an exaggerated vertical view of the heart of FIG. 25 elongated by the device of FIG. 27.
Figure 29:
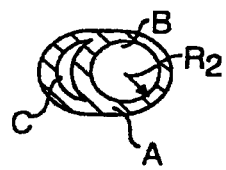
FIG. 29 is a view of the cross section of FIG. 26 showing the decrease in radius of the ventricles.

FIG. 28 is a vertical view of an elongate heart A having a horizontal width $W_2$ less than $W_1$. FIG. 29 is a horizontal cross section of the heart A of FIG. 28 including left ventricle B and right ventricle C. In FIG. 29, the radius $R_2$ of left ventricle B is less than $R_1$ of FIG. 26. Assuming that the hearts of FIGS. 25 and 28 are at the same point in the cardiac cycle, it can be appreciated that the wall stress in heart A is less in FIG. 29 as $R_2$ is shorter R.

If elongate bar 224 is sized such that device 220 does not engage at end diastole, but rather anchor pad 228 first engages during systolic contraction, device 220 can fall into a third class of device neither full cycle nor restrictive. Such a device would reduce wall stress during a portion of systolic contraction including end systole, but not reduce wall stress during end diastole, thus maintaining maximum preload.

Band 222 of device 220 is preferably formed from a web material or other fabric. Band 220 is preferably does not elongate substantially during diastolic filling. Members 224, 226 and 228 are formed from materials which remain substantially rigid under the influences of the forces encountered during the cardiac cycle.

Figures 30, 31:
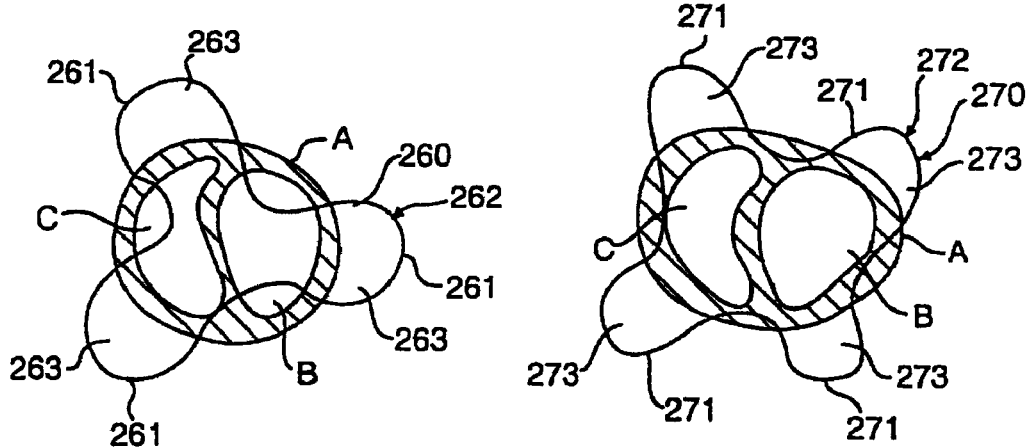
FIG. 30 is a horizontal cross sectional view of the left and right ventricles including reinforcement loops.
FIG. 31 is an alternate embodiment of the reinforcing loops of FIG. 30.

FIG. 30 is a horizontal cross sectional view of heart A including left ventricle B and right ventricle C. A device 260 including a thread or line 261 is disposed transventricularly and transmyocardially through heart A. A portion of line 261 is disposed outside of heart A. Opposite ends of line 261 are connected at 262. Those portions of line 261 outside heart A form loops 263. The size of loops 263 are exaggerated for purposes of illustration. It is assumed that heart A in the process of diastolic filling in FIG. 30, and loops 263 are sufficiently small, eventually heart A will engage loops 263. In such a configuration, device 260 is used as a restrictive device. Loops 263 could be sized, however, such that they engage full cycle.

Line 261 is preferably made from atraumatic biocompatible material. The diameter of line 261 is preferably sufficiently great that cutting of heart A does not occur during diastolic filling.

FIG. 31 is a horizontal cross sectional view of heart A including left ventricle B and right ventricle C and an alternate embodiment 270 of the device of FIG. 30. Device 270 includes a line 271 which does not extend transventricularly but extends through the myocardium of heart A to form four loops 273.

Device 270 can be formed from material similar to that used to form device 260. Additionally, device 270 can be made to function as a restrictive device or full cycle device in a manner similar to that of device 260.

Line 261 and line 267 could be disposed within a tube to avoid cheese cutting of the myocardium. The tube may be highly flexible, yet durable enough to prevent the line from cheese cutting through the myocardium of the heart. Devices 260 and 270 could extend through the septum or right ventricle to avoid forming lobes in right ventricle C.

Figure 32:
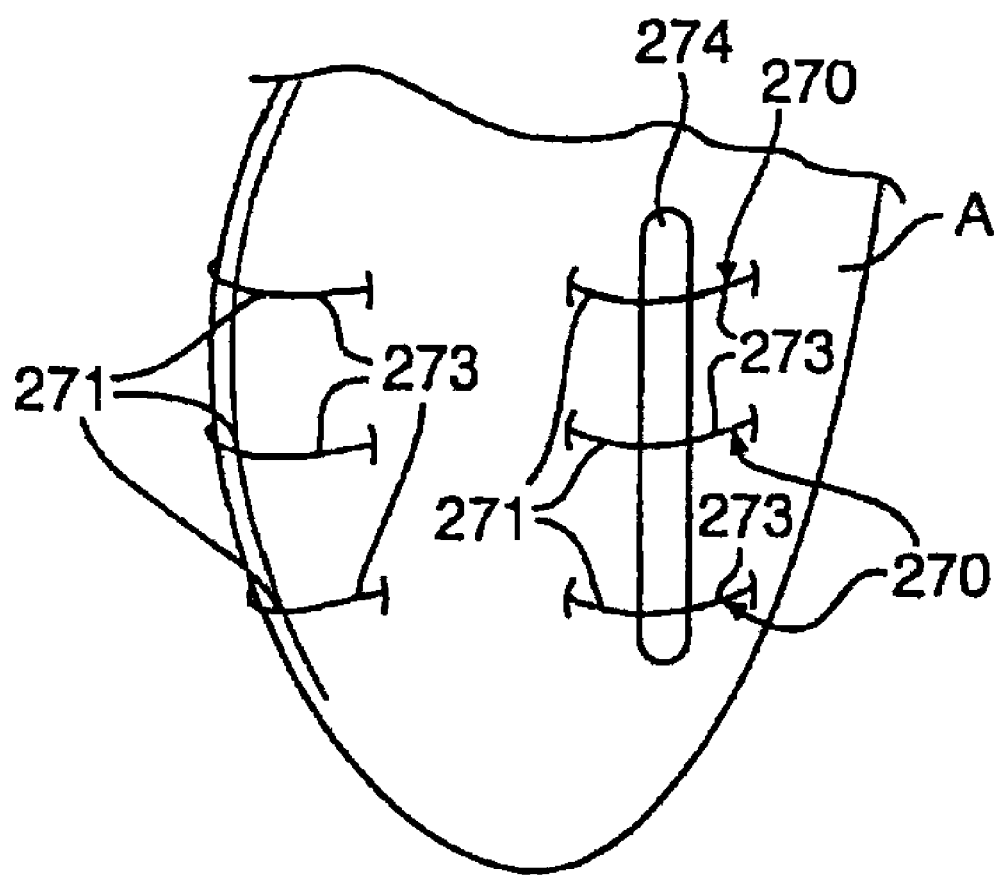
FIG. 32 shows a vertical view of the heart including the reinforcement loops of FIG. 31 and a rigid shape changing member.

FIG. 32 is a vertical view of heart A including three devices 270 disposed at three spaced elevations. An elongate generally rigid bar 274 is disposed through loops 273 to distribute the load on heart A from loops 273 across a larger area than lines 271 can alone.

It should be understood that although devices disclosed herein are described in relation to the left ventricle of a human heart, these devices could also be used to reduce the radius or cross-sectional area of the other chambers of a human heart in transverse or vertical directions, or at an angle between the transverse and vertical.

FIG. 33 shows a transverse cross-section of a left ventricle 10' and a right ventricle 12' of a human heart 14'. FIG. 33 also shows an embodiment of the present invention deployed with respect to left ventricle 10' of human heart 14'. Here a compression frame structure 300 is engaged with heart 14' at atraumatic anchor pads 310. A compression member 312 having an atraumatic surface 314 presses against a wall of left ventricle 10' to reduce the radius or cross-sectional area thereof.

FIG. 34 is a transverse cross-sectional view of human heart 14' showing yet another embodiment of the present invention. In this case a clamp 400 having atraumatic anchor pads 410 biased toward each other is shown disposed on a wall of left ventricle 10'. Here the radius or cross-sectional area of left ventricle 10' is reduced by clamping off the portion of the wall between pads 410. Pads 410 can be biased toward each other and/or can be held together by a locking device.

Each of the various embodiments of the present invention can be made from materials which can remain implanted in the human body indefinitely. Such biocompatible materials are well-known to those skilled in the art of clinical medical devices.

In use, the various embodiments of the present invention are placed in or adjacent the human heart to reduce the radius or cross-section area of at least one chamber of the heart. This is done to reduce wall stress or tension in the heart or chamber wall to slow, stop or reverse failure of the heart.

Figure 35:
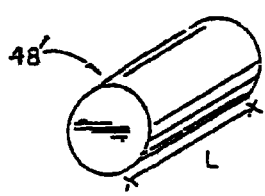
FIG. 35 is a idealized cylindrical model of a left ventricle of a human heart.

To discuss further the stress reduction associated with splinting, FIG. 35 is a view of a cylinder or idealized heart chamber 48' which is used to illustrate the reduction of wall stress in a heart chamber as a result of deployment of the splint in accordance with the present invention. The model used herein and the calculations related to this model are, intended merely to illustrate the mechanism by which wall stress is reduced in the heart chamber. No effort is made herein to quantify the actual reduction which would be realized in any particular in vivo application.

Figure 36:
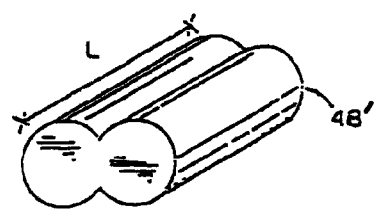
FIG. 36 is a splinted model of the left ventricle of FIG. 35.

FIG. 36 is a view of the idealized heart chamber 48' of FIG. 35 wherein the chamber has been splinted along its length L such that a "figure eight" cross-section has been formed along the length thereof. It should be noted that the perimeter of the circular transverse cross-section of the chamber in FIG. 35 is equal to the perimeter of the figure eight transverse cross-section of FIG. 36. For purposes of this model, opposite lobes of the figure in cross-section are assumed to be mirror images.

Figure 37:
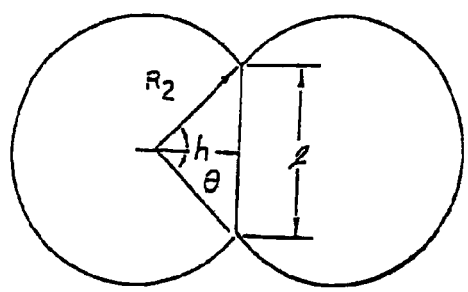
FIG. 37 is a transverse cross-sectional view of FIG. 36 showing various modeling parameters.

FIG. 37 shows various parameters of the figure eight cross-section of the splinted idealized heart chamber of FIG. 36. Where l is the length of the splint between opposite walls of the chamber, $R_2$ is the radius of each lobe, $\theta$ is the angle between the two radii of one lobe which extends to opposite ends of the portion of the splint within chamber 48' and h is the height of the triangle formed by the two radii and the portion of the splint within the chamber 48' ($R_1$ is the radius of the cylinder of FIG. 35). These various parameters are related as follows:

$h = R_2 \cos(\theta/2)$
$l = 2R_2 \sin(\theta/2)$
$R_2 = R_1 \pi/(2\pi - \theta)$ From these relationships, the area of the figure eight cross-section can be calculated by:

$$A_2 = 2\pi(R_2)^2(1 - \theta/2\pi) + hl$$

Where chamber 48' is unsplinted as shown in FIG. 35, $A_1$, the original cross-sectional area of the cylinder, is equal to $A_2$ where $\theta = 180°$, $h = 0$ and $l = 2R_2$. Volume equals $A_2$ times length L and circumferential wall tension equals pressure within the chamber times $R_2$ times the length L of the chamber.

Thus, for example, with an original cylindrical radius of four centimeters and a pressure within the chamber of 140 mm of mercury, the wall tension T in the walls of the-cylinder is 104.4 newtons. When a 3.84 cm splint is placed as shown in FIGS. 36 and 37 such that l=3.84 cm, the wall tension T is 77.33 newtons.

Figure 38:
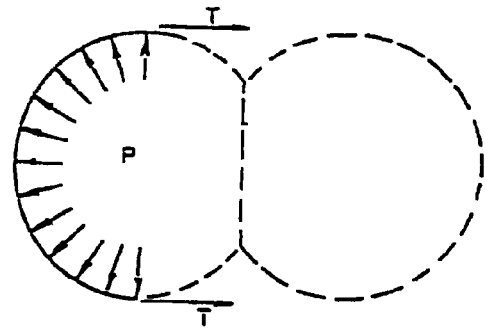
FIG. 38 is a transverse cross-section of the splinted left ventricle of FIG. 36 showing a hypothetical force distribution.
Figure 39:
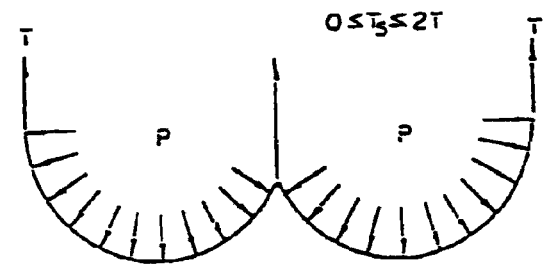
FIG. 39 is a second transverse cross-sectional view of the model left ventricle of FIG. 36 showing a hypothetical force distribution.

FIGS. 38 and 39 show a hypothetical distribution of wall tension T and pressure P for the figure eight cross-section. As $\theta$ goes from 180° to 0°, tension $T_\theta$ in the splint goes from 0 to a 2T load where the chamber walls carry a T load.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is defined in the language of the claims.

What is claimed is:

1. A method for improving the function of a heart, the method comprising:
   positioning a passive heart device relative to an external heart wall, the device including a wrap, a plurality of elongate anchors, and at least one flexible member extending from one of the plurality of elongate anchors;
   encircling a portion of the heart with the wrap, wherein the portion does not include an apex of the heart; and
   securing the device to the external heart wall by disposing a portion of the flexible member in heart tissue.

2. The method of claim 1, further comprising the step of exerting a compressive force on the external heart wall.

3. The method of claim 2, wherein exerting a compressive force on the external heart wall alters a geometric configuration of the heart.

4. The method of claim 3, wherein the geometric configuration is a shape of a heart chamber.

5. The method of claim 4, wherein the heart chamber is a left ventricle of the heart.

6. The method of claim 1, wherein encircling a portion of the heart with the wrap includes fully encircling the heart.

* * * * *